United States Patent [19]

Roe

[11] Patent Number: 5,422,169
[45] Date of Patent: Jun. 6, 1995

[54] ABSORBENT STRUCTURES CONTAINING SPECIFIC PARTICLE SIZE DISTRIBUTIONS OF SUPERABSORBENT HYDROGEL-FORMING MATERIALS IN RELATIVELY HIGH CONCENTRATIONS

[75] Inventor: Donald C. Roe, Cincinnati, Ohio

[73] Assignee: The Procter & Gamble Company, Cincinnati, Ohio

[21] Appl. No.: 149,173

[22] Filed: Nov. 8, 1993

Related U.S. Application Data

[63] Continuation of Ser. No. 684,633, Apr. 12, 1991, abandoned.

[51] Int. Cl.$^6$ .................. A61F 13/15; A61F 13/20; B32B 27/00
[52] U.S. Cl. .................. 428/212; 428/219; 428/283; 428/286; 428/288; 428/290; 428/302; 604/368; 604/375; 604/378
[58] Field of Search .................. 604/368, 378, 375; 428/72, 288, 286, 246, 212, 219, 283, 290, 302

[56] References Cited

U.S. PATENT DOCUMENTS

| | | |
|---|---|---|
| 32,649 | 3/1987 | Brandt et al. . |
| 3,347,236 | 10/1967 | Torr . |
| 3,654,929 | 4/1972 | Nilsson et al. . |
| 3,661,154 | 5/1972 | Torr . |
| 3,669,103 | 6/1972 | Harper et al. . |
| 3,670,731 | 6/1972 | Harmon . |
| 3,901,236 | 8/1975 | Assarsson et al. . |
| 3,932,322 | 1/1976 | Duchane . |
| 3,935,099 | 1/1976 | Weaver et al. . |
| 3,935,363 | 1/1976 | Burkholder et al. . |
| 3,971,373 | 7/1976 | Braun . |
| 3,993,551 | 11/1976 | Assarsson et al. . |
| 3,993,552 | 11/1976 | Assarsson et al. . |
| 3,993,553 | 11/1976 | Assarsson et al. ... |
| 4,023,571 | 5/1977 | Comerford et al. . |
| 4,055,184 | 10/1977 | Karami . |
| 4,058,124 | 11/1977 | Yen et al. . |
| 4,059,552 | 11/1977 | Zweigle et al. . |
| 4,102,340 | 7/1978 | Mesek et al. . |
| 4,103,058 | 7/1978 | Humlicek . |
| 4,105,033 | 8/1978 | Chatterjee et al. . |
| 4,115,332 | 9/1978 | Young et al. . |

(List continued on next page.)

FOREIGN PATENT DOCUMENTS

0080382A2 6/1983 European Pat. Off. .

(List continued on next page.)

OTHER PUBLICATIONS

Sanyo Chem. Ind. "Superabsorbent Plymer—SANWET IM-300/SANWET IM-1000" (1982).

(List continued on next page.)

*Primary Examiner*—James D. Withers
*Attorney, Agent, or Firm*—Jeffrey V. Bamber; Loretta J. Henderson; Bart S. Hersko

[57] ABSTRACT

Absorbent structures are disclosed which contain specific, relatively, narrow, particle size distributions of superabsorbent hydrogel-forming materials in relatively high concentrations. The absorbent structures of the present invention are useful in disposable absorbent articles such as diapers, adult incontinence pads, and the like. The absorbent articles of the present invention comprise a liquid pervious topsheet, a liquid impervious backsheet joined to the topsheet, and an absorbent core positioned between the topsheet and backsheet. At least a portion of the absorbent core comprises between about 25% and about 90% by weight particles of substantially water-insoluble, absorbent hydrogel-forming, polymer material formed by solution polymerization methods. The particles of the hydrogel-forming, polymer material are of such size that at least about 80% of the particles, by weight, will pass through a U.S. Standard 50 mesh sieve with 297 micron openings and be retained on a U.S. Standard 140 mesh sieve with 105 micron openings when the particles are tested according to the Sieving Test described herein.

46 Claims, 14 Drawing Sheets

U.S. PATENT DOCUMENTS

| | | |
|---|---|---|
| 4,123,397 | 10/1978 | Jones . |
| 4,124,748 | 11/1978 | Fujimoto et al. . |
| 4,134,863 | 1/1979 | Fanta et al. . |
| 4,145,464 | 3/1979 | McConnell et al. . |
| 4,155,893 | 5/1979 | Fujimoto et al. . |
| 4,172,066 | 10/1979 | Zweigle et al. . |
| 4,192,727 | 3/1980 | Ward . |
| 4,194,998 | 3/1980 | Fanta et al. . |
| 4,240,937 | 12/1980 | Allen . |
| 4,242,242 | 12/1980 | Allen . |
| 4,269,188 | 5/1981 | Nishizawa et al. . |
| 4,286,082 | 8/1981 | Tsubakimoto et al. . |
| 4,293,609 | 10/1981 | Erickson . |
| 4,327,728 | 5/1982 | Elias . |
| 4,333,464 | 6/1982 | Nakano . |
| 4,338,371 | 7/1982 | Dawn et al. . |
| 4,340,556 | 7/1982 | Ciencewicki . |
| 4,373,519 | 2/1983 | Errede et al. . |
| 4,381,782 | 5/1983 | Mazurak et al. . |
| 4,381,783 | 5/1983 | Elias . |
| 4,389,513 | 6/1983 | Miyazaki . |
| 4,401,795 | 8/1983 | Herman et al. . |
| 4,411,660 | 10/1983 | Dawn et al. . |
| 4,413,995 | 11/1983 | Korpman . |
| 4,429,001 | 1/1984 | Kolpin et al. . |
| 4,454,055 | 6/1984 | Richman et al. . |
| 4,460,642 | 7/1984 | Errede et al. . |
| 4,500,670 | 2/1985 | McKinley et al. . |
| 4,535,098 | 8/1985 | Evani et al. . |
| 4,536,181 | 8/1985 | Cook . |
| 4,551,191 | 11/1985 | Kock et al. . |
| 4,552,938 | 11/1985 | Mikita et al. . |
| 4,578,068 | 3/1986 | Kramer et al. . |
| 4,587,308 | 5/1986 | Makita et al. . |
| 4,604,313 | 8/1986 | McFarland et al. . |
| 4,610,678 | 9/1986 | Weisman et al. . |
| 4,625,001 | 11/1986 | Tsubakimoto et al. . |
| 4,645,789 | 2/1987 | Dabi . |
| 4,654,039 | 3/1987 | Brandt et al. . |
| 4,657,537 | 4/1987 | Zimmerer . |
| 4,666,975 | 5/1987 | Yamasaki et al. . |
| 4,666,983 | 5/1987 | Tsubakimoto et al. . |
| 4,670,011 | 6/1987 | Mesek ................................ 604/378 |
| 4,673,402 | 6/1987 | Weisman et al. . |
| 4,683,274 | 7/1987 | Nakamura et al. . |
| 4,685,909 | 8/1987 | Berg et al. . |
| 4,685,915 | 8/1987 | Hasse et al. . |
| 4,693,713 | 9/1987 | Chmelir et al. . |
| 4,699,823 | 10/1987 | Kellenberger et al. . |
| 4,718,899 | 1/1988 | Itoh et al. . |
| 4,732,968 | 3/1988 | Obayashi et al. . |
| 4,737,404 | 4/1988 | Jackson . |
| 4,834,735 | 5/1989 | Alemany et al. . |
| 4,888,231 | 12/1989 | Angstadt . |
| 4,892,533 | 1/1990 | Le-Khac . |
| 4,902,565 | 2/1990 | Brook . |
| 4,920,171 | 4/1990 | Hutton, Jr. et al. . |
| 4,923,454 | 5/1990 | Seymour et al. . |
| 4,935,022 | 6/1990 | Lash . |
| 4,948,818 | 8/1990 | Carmody et al. . |
| 4,973,632 | 11/1990 | Nagasuna et al. . |
| 4,988,344 | 1/1991 | Reising et al. . |
| 4,988,345 | 1/1991 | Reising . |
| 5,013,309 | 5/1991 | Baigas, Jr. et al. . |
| 5,015,245 | 5/1991 | Noda . |
| 5,047,023 | 9/1991 | Berg . |
| 5,061,259 | 10/1991 | Goldman et al. .................. 604/368 |
| 5,102,597 | 4/1992 | Roe et al. . |
| 5,124,188 | 6/1992 | Roe et al. ............................. 428/72 |
| 5,128,082 | 7/1992 | Makoui . |
| 5,147,345 | 9/1992 | Young et al. . |
| 5,149,334 | 9/1992 | Lahrman et al. . |
| 5,180,622 | 1/1993 | Berg et al. . |
| 5,217,445 | 6/1993 | Young et al. . |

FOREIGN PATENT DOCUMENTS

| | | |
|---|---|---|
| 156649 | 10/1985 | European Pat. Off. . |
| 198683 | 10/1985 | European Pat. Off. . |
| 0198683A2 | 10/1986 | European Pat. Off. . |
| 0202125A2 | 11/1986 | European Pat. Off. . |
| 216147 | 4/1987 | European Pat. Off. . |
| 0278601A2 | 8/1988 | European Pat. Off. . |
| 339461 | 11/1989 | European Pat. Off. . |
| 0389015A2 | 9/1990 | European Pat. Off. . |
| 0339564A2 | 11/1990 | European Pat. Off. . |
| 0339461A1 | 11/1991 | European Pat. Off. . |
| 0496594A2 | 7/1992 | European Pat. Off. . |
| 54-157788 | 12/1979 | Japan . |
| 56-65630 | 6/1981 | Japan . |
| 61-62463 | 3/1986 | Japan . |
| 1500559 | 2/1978 | United Kingdom . |
| 2113731A | 8/1983 | United Kingdom . |
| WO91/15177 | 10/1991 | WIPO . |
| WO91/15368 | 10/1991 | WIPO . |

OTHER PUBLICATIONS

Nippon Shokubai Kagaku Kogyo K.K. "Aqualic CA".
Stockhausen Inc., "Favor SAB-901" (1983).

(List continued on next page.)

OTHER PUBLICATIONS

BASF AG. "Luquasorb HC 9/80—Superabsorbent Based on Polyacrylic Acid or Aqueous Fluids".

Starchem GmbH, "Drystar" Technical Bulletin.

U.S. application Ser. No. 07/502,942, filed Apr. 2, 1990, Roe et al.

U.S. application Ser. No. 07/503,393, filed Apr. 2, 1990, Roe et al.

U.S. application Ser. No. 07/503,499, filed Apr. 2, 1990, Lahrman et al.

U.S. application Ser. No. 07/503,500, filed Apr. 2, 1990, Berg et al.

U.S. application Ser. No. 07/503,501, filed Apr. 2, 1990, Lahrman et al.

U.S. application Ser. No. 07/503,506, filed Apr. 2, 1990, Berg et al.

U.S. application Ser. No. 07/616,162, filed Nov. 20, 1990, Goldman et al.

U.S. application Ser. No. 07/625,774, filed Dec. 20, 1990, Lash.

U.S. application Ser. No. 07/625,775, filed Dec. 20, 1990, Young et al.

U.S. application Ser. No. 07/635,776, filed Dec. 20, 1990, Cook et al.

U.S. application Ser. No. 07/656,101, filed Feb. 11, 1991, Berg.

Z-Direction Test

X - Y Plane Test

ABSORBENT STRUCTURES CONTAINING SPECIFIC PARTICLE SIZE DISTRIBUTIONS OF SUPERABSORBENT HYDROGEL-FORMING MATERIALS IN RELATIVELY HIGH CONCENTRATIONS

This is a continuation of application Ser. No. 07/684,633, filed on Apr. 12, 1991, now abandoned.

FIELD OF THE INVENTION

The present invention relates to absorbent structures contain particulate superabsorbent hydrogel-forming materials. The absorbent structures of the present invention are particularly useful in disposable absorbent articles such as diapers, adult incontinence pads, and the like. More particularly, this invention relates to absorbent structures that have specific particle size distributions of superabsorbent hydrogel-forming materials in relatively high concentrations.

BACKGROUND OF THE INVENTION

The term "superabsorbent hydrogel-forming materials", as used herein, refers to substantially water-insoluble, absorbent, polymeric compositions that are capable of absorbing large quantities of fluids such as water and body exudates in relation to their weight and forming hydrogels thereby. Such materials are usually also capable of retaining such absorbed fluids under moderate pressures. Superabsorbent hydrogel-forming materials may also be referred to by other names such as "hydrocolloids", or "absorbent gelling materials".

The absorption characteristics of such superabsorbent hydrogel-forming materials, and cost of such materials, makes them especially useful for incorporation into absorbent articles, particularly disposable absorbent articles, such as disposable diapers. Some examples of the use of particulate superabsorbent hydrogel-forming materials in absorbent articles are disclosed in U.S. Pat. No. 3,699,103 issued to Harper et al. on Jun. 13, 1972 and U.S. Pat. No. 3,670,731 issued to Harmon on Jun. 20, 1972.

In the case of some disposable absorbent articles, it is desirable to produce a thinner product. Thinner products may provide user comfort and perception advantages. One way to produce thinner products while maintaining the overall fluid storage capacity of the product is to reduce the fiber weight content in the product's absorbent core while at the same time increasing the amount of particulate superabsorbent hydrogel-forming material in the core. This results in a product having a core with a higher weight concentration of particulate hydrogel-forming material.

However, in historical executions of absorbent articles containing high concentrations of superabsorbent materials (that is, greater than or equal to about 25% by weight), tradeoffs have been inevitable between providing such superabsorbent material concentrations and the fluid uptake and distribution rates of the absorbent articles. Disposable absorbent products containing high concentrations of standard bulk particle size distributions of particulate superabsorbent hydrogel-forming materials have the limitation that their rate of fluid uptake may be much lower than those of conventional cellulosic fiber webs. The term "fluid uptake rate" refers to the rate at which fluids are taken into the core in a direction that is into the plane of the absorbent article (that is, in the "z-direction"). This is particularly true in the case of particulate superabsorbent hydrogel-forming materials that have a relatively large average particle size.

The fluid uptake rate of such absorbent articles can be substantially increased by reducing the average size of the superabsorbent material particles in the product. However, when very small particles (or "fines") swell upon contact with liquids, the particles, when incorporated in a fiber web, tend to be easily forced into the interfiber capillaries of the web. The swollen or partially swollen fines may also form a mass of coagulated gel held together by fluid surface tension forces, thus forming a gel barrier. In either case, resistance to fluid flow through the structure is increased as fluid flow channels are blocked within the fiber web or by the gel mass, resulting in a marked decrease in permeability. These phenomena which interfere primarily with the transportation of fluids in the plane of the absorbent structure (in the "x-y" plane) are commonly referred to as "gel blocking." Further, because these absorbent articles are not able to process fluid (that is, to take in, distribute, and store fluids) rapidly or efficiently, there may be an increased probability of product failure.

There have been many efforts directed at solving the problems associated with incorporating superabsorbent materials into absorbent articles. For example, European Patent Application Publication number 0 339 461 published Nov. 10, 1985, in the name of Kellenberger, describes an effort directed to choosing a size of superabsorbent material that has a specific relationship to the pore size of an absorbent product. U.S. Pat. No. 4,699,823 issued Oct. 13, 1987, in the name of Kellenberger, et al. is directed to distribution of superabsorbent material in a positive concentration gradient through at least a portion of the thickness of an absorbent layer. Other efforts are directed at particle size e.g., U.S. Pat. No. 4,105,033, Chatterjee, et al. Many others mention particle sizes in various contexts, for instance U.S. Pat. Nos. 4,102,340, Mesek, et al.; 4,604,313, McFarland, et al.; and 4,666,975, Yamasaki, et al. However, none of the foregoing appear to have adequately understood and addressed the problems with the transport rate of fluids in both the x-y plane and in the z-direction.

The present invention seeks to resolve the above problems by providing improved absorbent structures and absorbent articles having high concentrations of particulate superabsorbent hydrogel-forming material, with improved fluid uptake and distribution rates.

SUMMARY OF THE INVENTION

The present invention provides high performance absorbent structures containing relatively high concentrations of particulate superabsorbent hydrogel-forming materials having specific, relatively narrow, particle size distributions. The absorbent structures of the present invention are particularly useful in disposable absorbent articles.

The absorbent articles of the present invention comprise a liquid pervious topsheet, a liquid impervious backsheet joined to the topsheet, and an absorbent core positioned between the topsheet and backsheet. The absorbent core at least partially comprises an absorbent structure of the present invention. The absorbent structure comprises a primary structure and a plurality of particles of substantially water-insoluble, absorbent hydrogel-forming, polymer material formed via solution polymerization methods. The particles of polymer material are distributed so that at least a 25 square centimeter portion of the absorbent structure (or the absorbent core) selected pursuant to the Weight Percentage Analysis described herein comprises between about 25% and about 90% by weight of the particles of polymer material. The particles of the polymer material are of such size that at least about 80% of said particles, by weight, will pass through a U.S. Standard 50 mesh sieve and be retained on a U.S. Standard 140 mesh sieve when said particles are tested according to the Sieving Test described herein.

The present invention is believed to overcome the fluid processing limitations of absorbent structures having higher concentrations of superabsorbent hydrogel-forming materials.

While not wishing to be bound by any particular theory, it is believed that the lack of the ability of the large particles to provide suitable fluid uptake rates is due to the small surface area to mass ratio characteristic of large particles of the superabsorbent hydrogel-forming material. The size of the superabsorbent material particles becomes especially important as the ratio of superabsorbent material to the other components of an absorbent structure increases, because the fluid processing and storage properties of the absorbent structure become more dependent on the characteristics of the superabsorbent material.

The surface area to mass ratio, and hence the fluid uptake rate, can be substantially increased by decreasing the average size of the particles in the bulk superabsorbent material composition. Because the narrow particle size fractions embodied in the absorbent structures of the present invention contain no large particles, the absorbent structures of the present invention are able to quickly take in and store fluids. Additionally, since the amount of very fine particles is reduced, the fluid distribution rates are significantly improved versus bulk particle size distributions.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

Figure 1:
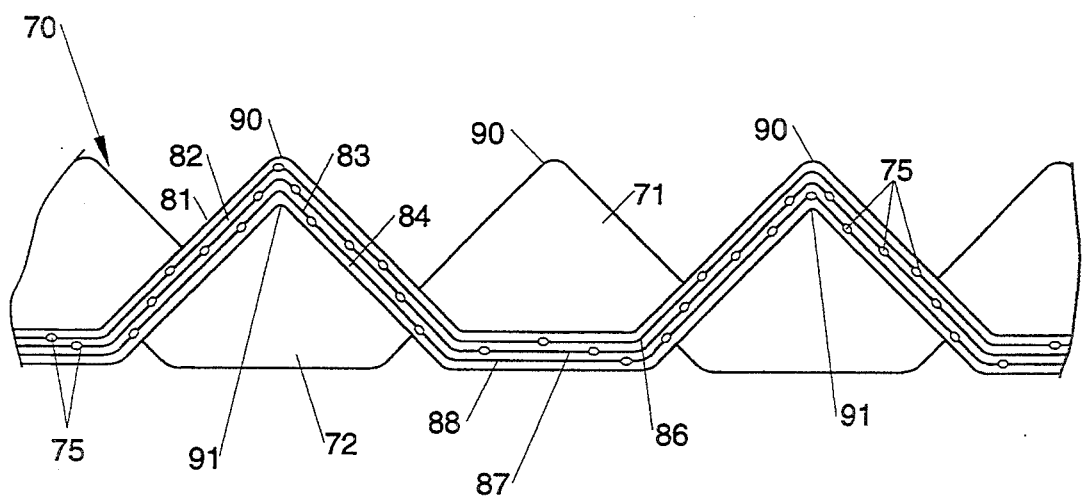
FIG. 1 is a fragmentary, enlarged cross-sectional view of a layered absorbent structure of the present invention.

The present invention provides absorbent structures that may be used in disposable absorbent products. The absorbent structures of the present invention contain a plurality of particles of superabsorbent hydrogel-forming material in relatively high concentrations. The superabsorbent material used in the absorbent structures of the present invention has a specific, relatively narrow, particle size distribution.

The absorbent structures of the present invention have higher fluid uptake and distribution rates than absorbent structures with standard bulk particle size distributions of particulate superabsorbent material. The term "standard bulk particle size distributions", as used herein, refers to those particle sizes in the range typically received from commercial superabsorbent material suppliers.

1. The Superabsorbent Hydrogel-Forming Materials Used Herein and the Absorbent Structures of the Present Invention.

A. The Superabsorbent Hydrogel-Forming Materials

The superabsorbent hydrogel-forming materials used in the present invention are substantially water-insoluble, absorbent, polymer materials that are capable of absorbing large quantities of fluids such as water and body exudates in relation to their weight and forming hydrogels in the process. Such materials are usually also capable of retaining such absorbed fluids under moderate pressures. Superabsorbent hydrogel-forming materials may also be referred to by other names such as simply "superabsorbent materials", or "hydrocolloids" or "absorbent gelling materials". The types of superabsorbent hydrogel-forming polymer materials useful in the present invention may vary widely.

The superabsorbent hydrogel-forming materials that are preferred for use in the present invention have an Absorptive Capacity (as measured by the test set forth herein) of at least about 18–20 grams, and more preferably at least about 25 grams, of Synthetic Urine per gram of the superabsorbent material (in its dry state). Typically, the superabsorbent hydrogel-forming materials used in the present invention will have an Absorptive Capacity of from about 30 to about 45 grams of Synthetic Urine per gram of superabsorbent material. Superabsorbent hydrogel-forming materials having Absorptive Capacities in this range are especially useful in absorbent structures and absorbent articles since they can hold high amounts of discharged body exudates such as urine under moderate confining pressures that simulate in-use conditions.

Some general types of suitable particulate superabsorbent hydrogel-forming polymer materials, and methods of making the same, useful in the present invention (although not limited to the specific particle size distributions described herein) are described in greater detail in U.S. Pat. No. Re. 32,649 entitled "Hydrogel-Forming Polymer Compositions For Use In Absorbent Structures" reissued to Brandt, et al. on Apr. 19, 1988.

The general types of particles suitable for use in the present invention may also be those particles that are referred to as "precursor" particles in the following U.S. patent applications: Ser. No. 07/502,942 entitled "Particulate Polymeric Compositions Having Interparticle Crosslinked Aggregates of Fine Precursors" filed in the names of Donald Carroll Roe, et al., now U.S. Pat. No. 5,384,179; Ser. No. 07/503,393 entitled "Porous, Absorbent, Polymeric Macrostructures and Method of Making the Same" filed in the names of Donald Carroll Roe, et al., now U.S. Pat. No. 5,124,188; Ser. No. 07/503,499 entitled "Method for Producing Polymeric Compositions Containing Interparticle Crosslinked Aggregates" filed in the names of Frank Henry Lahrman, et al., now Ser. No. 08/225,947, pending; Ser. No. 07/503,500 entitled "Absorbent Members Containing Interparticle Crosslinked Aggregates" filed in the names of Charles John Berg, et al., now U.S. Pat. No. 5,190,622; Ser. No. 07/503,501 entitled "Absorbent Articles Containing Interparticle Crosslinked Aggregates" filed in the names of Frank Henry Lahrman, et al., now U.S. Pat. No. 5,149,334; Ser. No. 07/503,506 entitled "Particulate, Absorbent, Polymeric Compositions Containing Interparticle Crosslinked Aggregates" filed in the names of Charles John Berg, et al., now U.S. Pat. No. 5,300,565, all filed Apr. 2, 1990. These pending patent applications may be referred to collectively as the "Inter-Particle Crosslinked Aggregate" patent applications. The disclosures of the Brandt, et al. patent and all of these pending applications are incorporated by reference herein.

The superabsorbent hydrogel-forming material particles may optionally be surface treated as described in the aforementioned Inter-Particle Crosslinked Aggregate patent applications. Thus, the superabsorbent material particles may be surface treated as described in U.S. Pat. No. 4,824,901 issued to Alexander et al. on Apr. 25, 1989, the disclosure of which is incorporated by reference herein. If surface treated, the superabsorbent material particles are preferably surface crosslinked as disclosed in U.S. Pat. No. 4,666,983, entitled "Absorbent Article", issued to Tsubakimoto et al. on May 19, 1987; and U.S. Pat. No. 4,734,478, entitled "Water Absorbing Agent" issued to Tsubakimoto et al. on Mar. 29, 1988; the disclosures of which are incorporated by reference herein. As disclosed in the Tsubakimoto et al. '983 patent, the superabsorbent material particles may be surface crosslinked by applying a surface crosslinking agent onto the particles and reacting the surface crosslinking agent with the polymer material at or near or in the proximity of the surface of the particles.

The superabsorbent hydrogel-forming materials may also have the level of extractable polymer material specified in the aforementioned patent issued to Brandt, et al.

The preferred polymer materials for use as the superabsorbent hydrogel-forming material particles possess a carboxyl group. These polymers include hydrolyzed starch-acrylonitrile graft copolymers, partially neutralized starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked products of any of the foregoing copolymers, partially neutralized polyacrylic acid, and slightly network crosslinked products of partially neutralized polyacrylic acid. These polymers may be used either independently or in the form of a mixture of two or more monomers, compounds, or the like. Examples of these polymer materials are disclosed in U.S. Pat. Nos. 3,661,875; 4,076,663; 4,093,776; 4,666,983; and 4,734,498, the disclosures of which are all incorporated by reference herein.

The most preferred polymer materials for use as the superabsorbent hydrogel-forming material particles are slightly network crosslinked products of partially neutralized polyacrylic acids and starch derivatives therefrom. Most preferably, the particles comprise from about 50 to about 95%, preferably about 75%, neutralized, slightly network crosslinked, polyacrylic acid (e.g., poly (sodium acrylate/acrylic acid)).

The individual particles of polymer material may be formed in any conventional manner. Typical and preferred processes for producing the particles are described in: U.S. Pat. No. Re. 32,649 reissued to Brandt, et al. on Apr. 19, 1988; U.S. Pat. No. 4,666,983 entitled "Absorbent Article" issued to Tsuneo Tsubakimoto, Tadao Shimomura, and Yoshio Irie on May 19, 1987; and U.S. Pat. No. 4,625,001 entitled "Method For Continuous Production Of Cross-Linked Polymer" issued to Tsuneo Tsubakimoto, Tadao Shimomura, and Yoshio Irie on Nov. 25, 1986. The disclosures of these patents are incorporated by reference herein.

The preferred methods for forming the particles are those that involve aqueous solution or other solution polymerization methods as opposed to reverse phase polymerization (the latter also being known as "inverse phase polymerization" or "emulsion polymerization"). As described in the above-referenced U.S. Pat. No. Re. 32,649, aqueous solution polymerization involves the use of an aqueous reaction mixture to carry out polymerization to form the particles.

The superabsorbent hydrogel-forming materials incorporated into the absorbent structures of the present invention are in a particulate form. The term "particulate" is used herein to mean that the superabsorbent hydrogel-forming materials are in the form of discrete units denominated "particles". The particles can comprise granules, pulverulents, spheres, aggregates or agglomerates. However, typically, the particles described herein will be largely non-aggregated. The particles can have any desired shape such as cubic; polyhedral; spherical; rounded; angular; irregular; or randomly-sized irregular shapes (e.g., pulverulent products of a grinding or pulverizing step).

The size distribution of the particles of superabsorbent hydrogel-forming material is of critical importance to the performance of absorbent structures. This is particularly true in the case of absorbent structures containing relatively high concentrations of the particulate superabsorbent hydrogel-forming material. The impact of the superabsorbent hydrogel-forming material particles on the overall fluid uptake and distribution of the absorbent structure is significantly increased at higher concentrations because there is less fiber to compensate for any adverse effects on fluid acquisition and distribution rates and storage capacity caused by the superabsorbent material.

Large particles of superabsorbent hydrogel-forming materials swell very slowly and significantly decrease the potential fluid uptake rate (that is, the rate at which fluid is taken into the absorbent structure in the z-direction). Very small particles (or "fines") tend to swell rapidly, but are easily forced into capillary spaces, decreasing the structure's permeability and dramatically curtailing the rate of fluid distribution throughout the structure, particularly in the x-y plane. Also, high concentrations of fine particles can often coagulate into a gel mass that acts as a barrier to fluid distribution. These are the phenomena associated with fine particles that are referred to above as "gel-blocking".

By using a specific, relatively narrow, particle size distribution in absorbent structures having high concentrations of superabsorbent hydrogel-forming material, the above-mentioned fluid processing limitations of both large and fine particles can be significantly reduced or eliminated. While not wishing to be bound by any particular theory, it is believed that the average particle size largely determines the potential fluid uptake rate of an absorbent article. This is true because the fluid uptake rate is dependent on the overall surface area per unit mass of the superabsorbent hydrogel-forming material. The range of particle sizes (or "breadth of the distribution" of the particle size) impacts both the potential fluid uptake rate and the distribution rate of the structure. Ideally, the breadth of distribution of particle sizes should be very small.

This invention relates to the use of particle size distributions centered in the range of about 125–300 microns, with an average particle size of about 125–250 microns being most preferred. The breadth should be such that at least about 95% of the particles are within 100 microns of the average particle size, (but within 75 microns of the average particle size at the lower end of the above ranges). The most preferred execution would involve at least about 95% by weight of the superabsorbent hydrogel-forming material being within 75 microns of the average particle size.

The specific size distribution of the superabsorbent hydrogel-forming material used in the present invention can be expressed by using the actual dimensions of the particles. A method suitable for determining the actual dimensions of the particles is set forth in greater detail in several of the Inter-Particle Crosslinked Aggregate patent applications, the disclosures of which were incorporated by reference above. However, determining the actual particle dimensions can be a relatively complicated process due to the different shapes and dimensions that such particles may have. Therefore, for simplicity, the particle sizes in the absorbent structures of the present invention are expressed in another manner.

For purposes of the present invention, the term "particle size" is defined as the dimension of a particle which is determined by a sieve size analysis according to the Sieving Test described in greater detail herein. A sample of particles is sieved as described, and the results are recorded. It should be understood that for particles that are not spherical, the sieving test may determine the size of only certain dimensions of a specific particle. The results of such a sieve size analysis, however, sufficiently define the size of the particles for the purposes of the present invention. The results of the sieve analysis may be expressed by two equivalent conventions in terms of the characteristics of the sieves used.

One way to express the size of the particles is in terms of the size of the openings in the sieves. For instance, in principal, a particle that is retained on a sieve with 149 micron openings is considered to have a particle size greater than or equal to 149 microns for the purposes of the present invention. A particle that passes through a sieve with 297 micron openings and is retained on a sieve with 149 micron openings is considered to have a particle size between 149 and 297 microns. A particle that passes through a sieve with 149 microns is considered to have a particle size less than 149 microns.

The other way to express the size of the particles in terms of the results of a sieving analysis, is in terms of the designation used for the sieves. For example, a particle that passes through a U.S. Standard #50 sieve and is retained on a Standard #100 sieve is considered to be of a 50/100 mesh size. In preferred embodiments of this invention, the specific particle size distributions employed include, but are not limited to the following: 35/170 mesh, 35/140 mesh, 35/120 mesh, 40/100 mesh, 40/120 mesh, 40/140 mesh, 40/170 mesh, 50/170 mesh, 50/140 mesh, 50/120 mesh, 50/100 mesh, 45/120 mesh, 45/140 mesh, 45/170 mesh, 45/100 mesh, 60/100 mesh, 60/120 mesh, 50/70 mesh, 60/80 mesh, and 70/100 mesh. In the most preferred executions, 50/100 mesh, 50/120 mesh, 50/140 mesh, 50/170 mesh, 45/120 mesh, 45/140 mesh, 60/100 mesh, 60/120 mesh, 50/70 and 60/80 mesh particle size distributions are used.

The results described in either of the foregoing manners can be easily described in the other way by referring to a sieve size chart and locating the corresponding value. Such a sieve size chart is found in Table 21-6 of *Perry's Chemical Engineers' Handbook, Sixth Edition*, (McGraw-Hill Book Company, 1984) at page 21-15, which publication is incorporated by reference herein. Thus, the preferred particle sizes referred to above expressed in terms of sieve size openings can be summarized in the following table. (It should be understood, however, that the lower numbers in each of the mesh designations in the left hand column of the following table correspond to the larger particle sizes in the ranges listed in the column on the right side of the table.)

TABLE 1

RANGES OF PARTICLE SIZES EXPRESSED IN TERMS OF SIEVE SIZE

| Particle Size Expressed in Terms of U.S. Sieve Series | Particle Size Expressed in Terms of Sieve Opening Sizes (microns) |
| --- | --- |
| 35/170 mesh | 88–500 |
| 35/140 mesh | 105–500 |
| 35/120 mesh | 125–500 |
| 40/170 mesh | 88–420 |
| 40/140 mesh | 105–420 |
| 40/120 mesh | 125–420 |
| 40/100 mesh | 149–420 |
| 45/170 mesh | 88–354 |
| 45/140 mesh | 105–354 |
| 45/120 mesh | 125–354 |
| 45/100 mesh | 149–354 |
| 50/170 mesh | 88–297 |
| 50/140 mesh | 105–297 |
| 50/120 mesh | 125–297 |
| 50/100 mesh | 149–297 |
| 50/70 mesh | 210–297 |
| 60/120 mesh | 125–250 |

TABLE 1-continued

RANGES OF PARTICLE SIZES EXPRESSED IN TERMS OF SIEVE SIZE

| Particle Size Expressed in Terms of U.S. Sieve Series | Particle Size Expressed in Terms of Sieve Opening Sizes (microns) |
|---|---|
| 60/100 mesh | 149–250 |
| 60/80 mesh | 177–250 |
| 70/100 mesh | 149–210 |

It is well known that in most sieving analyses, certain particles may pass through or be retained on a sieve in one test, and not on another identical test. This can result from the shape of the particle and the different orientation relative to the sieve openings the particle may assume in each test. Because of this, the test results are generally expressed in terms of the percentage of particles, by weight, that will ordinarily pass through a sieve of one dimension and be retained on a sieve of a second dimension. For example, in one embodiment of the present invention, at least about 85% of the particles by weight, will pass through a U.S. Standard 50 mesh sieve with 297 micron openings and be retained on a U.S. Standard 140 mesh sieve with 105 micron openings when the particles are tested according to the Sieving Test. Preferably, in the present invention, no more than about 10%, most preferably no more than about 5% by weight of the particles should be larger than a 50 mesh screen or smaller than a 140 mesh screen.

The specific particle size distributions described above can be prepared by any suitable method. The specific particle size distributions can be prepared, at least in relatively small amounts by a sieving operation.

B. The Absorbent Structures of the Present Invention

The superabsorbent hydrogel-forming materials in the particle size ranges described above can be employed in combination with other materials to form improved absorbent structures, such as those shown in FIGS. 1–11. The absorbent structures of the present invention will be described herein in relationship to their use in absorbent articles; however, it should be understood that the potential application of the absorbent structures should not be limited to the specific absorbent articles described herein.

The absorbent structures of the present invention are articles that are capable of absorbing and retaining liquids. These liquids can be, but are not limited to water and certain body exudates. Preferably, when used in absorbent articles of the type described in Section 2 below, the absorbent structures are generally compressible, conformable, and non-irritating to the skin.

The materials used to form the absorbent structures of the present invention can be in any structural form, provided that structure is capable of transporting liquids between its structural elements. The term "structural elements", as used herein, refers to the individual fibers, yarns, strands, loose particles, and the like which may comprise the above structure.

Typically, the absorbent structures of the present invention at least partially comprise some type of primary structure. The term "primary structure", as used herein, is the structure or matrix that the particles of superabsorbent material may be located or dispersed in, or on, when the particles of superabsorbent material are incorporated into an absorbent structure.

The primary structure will typically define the dimensions of the absorbent structure of the present invention. Therefore, when the particles of superabsorbent material is described herein as being distributed in a certain manner relative the absorbent structure, they will generally be distributed in a like manner relative to the primary structure.

The absorbent structures of the present invention preferably comprise a primary structure, such as a web, batt, or other mixture of fiber material with specific quantities of the particulate superabsorbent hydrogel-forming materials described herein. Such webs typically comprise entangled masses of fibers (in other words, fibrous or fiber material). It should be understood, however, that for the purposes of this invention an absorbent structure is not necessarily limited to a web or the like in the form of a single layer or sheet of material. Thus, an absorbent structure may actually comprise laminates, webs, or combinations of several sheets or webs of the types of materials as hereinafter described. Thus, as used herein, the term "structure" includes the term "structures" and the terms "layers" or "layered."

Various types of fiber material can be used in the absorbent structures of the present invention. Any type of fiber material which is suitable for use in conventional absorbent products is also suitable for use in the absorbent structures described herein. Specific examples of such fiber materials include cellulose fibers, modified cellulose fibers, rayon, polypropylene, and polyester fibers such as polyethylene terephthalate (DACRON), hydrophilic nylon (HYDROFIL), and the like. Other fiber materials include cellulose acetate, polyvinyl flouride, polyvinylidene chloride, acrylics, polyvinyl acetate, polyamides (such as nylon), bicomponent fibers, tricomponent fibers, mixtures thereof, and the like. Hydrophilic fiber materials, however, are preferred.

The term "hydrophilic", as used herein, describes fibers or the surfaces of fibers which are wetted when liquids are deposited onto the fibers. (That is, a fiber or its surface is considered to be hydrophilic if water or aqueous body liquids readily spreads on or over the surface of the fiber without regard to whether or not the fiber actually imbibes the fluid or forms a gel). The state of the art respecting wetting of materials defines hydrophilicity (and wetting) in terms of contact angles and the surface tension of the liquids and solids involved. This is discussed in detail in the American Chemical Society Publication entitled *Contact Angle Wettability, and Adhesion* edited by Robert F. Gould and copyrighted in 1964, which publication is incorporated by reference herein.

Examples of suitable hydrophilic fiber materials, in addition to some already mentioned, are hydrophilized hydrophobic fibers. These include surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent products, may be suitable for use in the absorbent structures of the present invention due to their good wicking properties. This is because the wicking propensity of the fibers is as important, if not more important, than the absorbent capacity of the fiber material itself. This is due to the high rate of fluid uptake and lack of gel blocking properties of the particulate superabsorbent hydrogel-forming materials used in the absorbent structures of the present invention. Hydrophobic synthetic fibers can also be used, but are less preferred.

For reasons of availability and cost, cellulose fibers are generally preferred for use as the hydrophilic fiber material of the absorbent structures described herein. Most preferred are wood pulp fibers which are referred to as "airfelt".

Other cellulosic fiber materials which may be useful in some of the absorbent structures described herein are chemically stiffened cellulosic fibers. Preferred chemically stiffened cellulosic fibers are the stiffened, twisted, curled cellulosic fibers which can be produced by internally crosslinking cellulose fibers with a crosslinking agent. The types of stiffened, twisted, curled cellulosic fibers useful as the hydrophilic fiber material of the absorbent structures described herein are described in greater detail in the following patents: U.S. Pat. No. 4,822,453 entitled "Absorbent Structure Containing Individualized Crosslinked Fibers", issued to Dean et al. on Apr. 18, 1989; U.S. Pat. No. 4,888,093 entitled "Individualized, Crosslinked Fibers And Process For Making Said Fibers", issued to Dean et al. on Dec. 19, 1989; U.S. Pat. No. 4,889,595 entitled "Process For Making Individualized, Crosslinked Fibers Having Reduced Residuals And Fibers Thereof", issued to Herron et al. on Dec. 26, 1989; U.S. Pat. No. 4,889,596 entitled "Process For Making Individualized Crosslinked Fibers And Fibers Thereof", issued to Schoggen et al. on Dec. 26, 1989; U.S. Pat. No. 4,889,597 entitled "Process For Making Wet-Laid Structures Containing Individualized Stiffened Fibers", issued to Bourbon et al. on Dec. 26, 1989; and U.S. Pat. No. 4,898,642 entitled "Twisted, Chemically Stiffened Cellulosic Fibers And Absorbent Structures Made Therefrom", issued to Moore et al. on Feb. 6, 1990. The disclosures of each of these patents is hereby incorporated by reference herein.

The relative amount of fiber (or other suitable type of) material and particulate superabsorbent hydrogel-forming materials used in the absorbent structures of the present invention can be most conveniently expressed in terms of the weight percentage of those components in the absorbent structure. The absorbent structures preferably contain from about 10% to about 98% overall, by weight of the absorbent structure, of the particulate superabsorbent material. This concentration of the particulate superabsorbent material can also be expressed in terms of a weight ratio of fiber (or other material) to the superabsorbent material. This ratio may range from about 90:10 to about 2:98. For most absorbent structures, the optimum overall fiber-to-particulate weight ratio is in the range of from about 90:10 to about 15:85.

The superabsorbent material may be substantially uniformly dispersed (thoroughly dispersed) throughout the entire absorbent structure as disclosed in U.S. Pat. No. 4,610,678 entitled "High-Density Absorbent Structures" issued to Paul T. Weisman and Stephen A. Goldman on Sep. 9, 1986, the disclosure of which is incorporated by reference herein.

In other absorbent structures, the superabsorbent hydrogel-forming material may be dispersed in various weight ratios throughout different regions and throughout the thickness of the absorbent structure. For example, the mixture of fiber material and the particulate superabsorbent hydrogel-forming material may be disposed only in certain portions of the absorbent structure.

The superabsorbent material may alternatively be distributed in regions or zones which have higher concentrations of the superabsorbent material than do other regions or zones. For example, European Patent Application Publication Number 0 198 683, published Oct. 22, 1986 in the name of Duenk, et al. and U.S. Pat. No. 4,699,823 issued to Kellenberger et al. on Oct. 13, 1987, disclose absorbent structures having a superabsorbent material distributed in a positive gradient through at least a portion of the thickness of the absorbent structure. The disclosures of both of the aforementioned patent publications are incorporated by reference herein.

Regardless of homogeneity of the distribution of the superabsorbent hydrogel-forming material in the specific product design, the desired superabsorbent material weight percentage in this invention is between about 25% and about 98% of the absorbent structure. The weight percentage of superabsorbent material may fall within any narrower range that lies within the above range. Such narrower ranges include, but are not limited to the ranges of: between about 25% and about either 70%, 75%, 80%, 85%, or 90%. Some specific percentages of hydrogel-forming material useful in the present invention that fall within the above ranges, include, but are not limited to weight percentages of: 35%, 50%, and 70%.

For the purposes of the present invention, an absorbent structure will be considered to have the weight percentage specified in the appended claims if that weight percentage can be found in at least one 25 square centimeter portion of the absorbent structure. The 25 square centimeter portion is selected according to the test for determining the weight percentage of superabsorbent material provided below.

Weight Percentage Analysis

The weight percentage is measured by die-cutting a representative portion of the absorbent structure to obtain a sample. The term "representative portion", as used herein, refers to a portion of the structure which contains superabsorbent material and is characteristic of the portion of the absorbent structure which contains the highest concentration of superabsorbent material.

The representative portion is cut with a die capable of cutting a sample 25 square centimeters in area. The die can be of any shape as long as no dimension of the area cut by the die exceeds 8.5 cm.

The representative portion of the absorbent structure may be located in various different locations in a given absorbent structure. By way of example, if the absorbent structure is in the core (or other absorbent component) of a diaper or other absorbent article, the representative portion will typically be found in an area of the core that can be defined within the boundaries of a rectangular-shaped area that is centered about the longitudinal centerline of the absorbent article and has dimensions of about 2.5 inches × 10 inches (about 6.4 cm. × about 25 cm.).

This rectangular-shaped area is positioned so that the longer sides of the rectangular-shaped area run in the same direction as the longitudinal centerline of the absorbent article. One of the shorter edges of the rectangular-shaped area (hereinafter referred to as the "top edge") will be adjacent to the front end edge of the core. The "front end edge" of the core is the transverse edge of the core that is to the wearer's front when the absorbent article is worn. This top edge of the rectangular-shaped area should be spaced a distance of about 1 inch (about 2.54 cm.) from the front end edge of the core. However, it should be understood that the location of the representative portion of a diaper or other absorbent article is not limited to this rectangular-shaped area.

The section of the absorbent structure from which the 25 square centimeter sample is taken should be cut completely through in order to obtain the sample. However, if the absorbent structure comprises more than one discrete layer or zone (such as, and by way of example only, in the case of the embodiment of the present invention shown in FIG. 7 which has an acquisition layer positioned over a storage layer), separate samples shall be obtained in those layers or zones.

If a sample obtained from any one of such layers or zones contains superabsorbent material that is within the specified weight percentage, then the absorbent structure will be considered to have a portion that is within such weight percentage. This is the case regardless of whether the other layers or zones contain the specified weight percentage. The above method is intended to be applied in reasonable manner to obtain a truly representative sample of the absorbent structure in issue without any deliberate attempts to exclude portions of a given absorbent structure which might otherwise fall within the scope of the appended claims.

The density of the absorbent structures described herein can also be important in several respects. It can be important in determining the absorbent properties of the absorbent structures by themselves and the absorbent properties of the articles in which such absorbent structures may be employed. The density of the absorbent structures described herein will generally be in the range of from about 0.06 g/cm$^3$ to about 0.5 g/cm$^3$, and more preferably within the range of from about 0.08 g/cm$^3$ to about 0.35 g/cm$^3$. Density values for these structures are calculated from their basis weight and caliper. Caliper is measured under a "gentle" load of 10 grams/cm$^2$. The basis weight is measured by die-cutting a certain size sample and weighing the sample on a standard scale. The weight and area of the sample determine the basis weight. The density and basis weight values include the weight of the particles of the superabsorbent hydrogel-forming material.

The absorbent structures of the present invention can contain a variety of optional materials in addition to the fiber (or other suitable) materials and the superabsorbent hydrogel-forming materials. Such optional materials can include, for example, fluid distribution aids, antimicrobials, pH control agents, odor control agents, perfumes, etc. If present, these optional components should generally comprise no more than about 30% by weight of the absorbent structures.

The preferred fibrous absorbent structures described herein can be prepared by any process or technique that provides a web that comprises a combination of fibers and particles of superabsorbent hydrogel-forming material. These absorbent structures are preferably formed by air-laying a substantially dry mixture of fibers and superabsorbent hydrogel-forming material particles and, if desired or necessary, densifying the resulting web. Such a procedure is described more fully in U.S. Pat. No. 4,610,678, the disclosure of which was previously incorporated by reference herein. As indicated in U.S. Pat. No. 4,610,678, the air-laid webs formed by this procedure will preferably comprise substantially unbonded fibers. These webs will preferably have a moisture content of 10% or less.

In one alternative embodiment of the present invention, the absorbent structure may comprise a laminate (a layered absorbent structure) that contains at least one, and optionally two or more, layers of dispersed particles of the superabsorbent hydrogel-forming material. Such a laminate preferably comprises layers or webs of fibrous materials.

The term "web of fibrous material", as used herein, is a sheet of thin, substantially contiguous material having two substantially parallel surfaces. Although a web of fibrous material need not be flat or smooth, theoretically, it is or can be laid out in a substantially planar, two-dimensional arrangement of indefinite length and indefinite width projecting in the two dimensions. Examples of webs of fibrous materials used in the layered absorbent structures of the present invention include many papers and nonwoven materials. The webs of fibrous materials used in the present invention are preferably webs of absorbent materials, more preferably webs of absorbent papers, most preferably absorbent tissue. The webs of fibrous materials may all be the same fibrous material or may be different fibrous materials.

Several types of layered absorbent structures are more fully described in U.S. Pat. No. 4,578,068 entitled "Absorbent Laminate Structure" issued to Timothy A. Kramer, Gerald A. Young and Ronald W. Kock on Mar. 25, 1986, the disclosure of which patent is hereby incorporated by reference herein. Methods and apparatus for making such laminates are described in U.S. Pat. No. 4,551,191 entitled "Method For Uniformly Distributing Discrete Particles On A Moving Porous Web", issued to Ronald W. Kock and John A. Esposito on Nov. 5, 1985, the disclosure of which patent is also hereby incorporated by reference herein.

Preferably, if the absorbent structure of the present invention comprises a laminate, the particles of superabsorbent hydrogel-forming materials are distributed in at least a portion of such an absorbent structure in a concentration of at least about 35% by weight, more preferably, in at least about 40% by weight of the absorbent structure.

FIG. 1 shows an exemplary embodiment of a laminate of the present invention, layered absorbent structure 70. The layered absorbent structure 70 of the present invention has an upper surface 71 and a lower surface 72. The preferred layered absorbent structure 70 shown in FIG. 1 comprises four webs of fibrous material: uppermost web 81, lowermost web 84, and intermediate webs 82 and 83. The layered absorbent structure 70 has interfaces 86, 87 and 88 between adjacent webs with the particles 75 of the particulate superabsorbent hydrogel-forming, material forming a discontinuous layer at each of the interfaces 86, 87 and 88. As shown in FIG. 1, the layered absorbent structure 70 further preferably has conical protrusions 90 in the upper surface 71 and corresponding conical concavities 91 in the lower surface 72.

The webs of fibrous materials are preferably frangibly bonded together in the layered absorbent structures 70 of the present invention (that is, the bonds are relatively easily broken). The bonding can be substantially entirely by fiber entanglement between contacting surfaces of adjacent webs at interfaces where the particles 75 are present.

The particles of superabsorbent material 75 may be held in place in various different ways. For example, the particles 75 may be immobilized at the interfaces 86, 87, and 88 by fiber entrapment. Alternatively, the particles 75 of the superabsorbent hydrogel-forming material may be bonded in several different manners to one or more of the webs. Preferably, whatever way the particles 75 are held in place, they should be able to swell freely. This will permit the greatest amount of the capacity of the superabsorbent material to be used. An exemplary process for producing such layered absorbent structures is described in U.S. Pat. No. 4,578,068, previously incorporated by reference herein.

Another alternative embodiment of the layered absorbent structures of the present invention is a "pouch" containing the particulate superabsorbent hydrogel-forming material. The pouch can be a layered absorbent structure as described above in which the number of fibrous webs equals two. The fibrous webs are joined to each other around their periphery to form a large pocket in the middle of the pouch. The particles 75 of the superabsorbent material are encased between the 20 fibrous webs in the pocket. The pouch is, thus, similar to a tea bag in that the particulate superabsorbent hydrogel-forming material is free to swell and absorb within the pouch. The fibrous webs of the pouch preferably comprise any nonwoven material known in the art. The nonwoven webs can be heat sealed about their periphery, although any other means for sealing the webs together known in the art, such as adhesives or ultrasonic bonds, may also be used.

2. Use of the Absorbent Structures in Absorbent Articles

A. In General

The absorbent structures of the present invention, such as absorbent structure 70, are especially suitable for use both in and as absorbent cores in absorbent articles, especially disposable absorbent articles.

The term "absorbent article", as used herein, refers to articles which absorb and contain body exudates and other fluids. More specifically, the term "absorbent article", as used herein, generally refers to articles which are placed against or in proximity to the body of the wearer to absorb and contain the various exudates discharged from the body. The term "disposable absorbent articles", as used herein, are those absorbent articles which are intended to be discarded after a single use (i.e., the original absorbent article in whole is not intended to be laundered or otherwise restored or reused as an absorbent article, although certain materials or all of the absorbent article may be recycled, reused, or composted).

Figure 2:
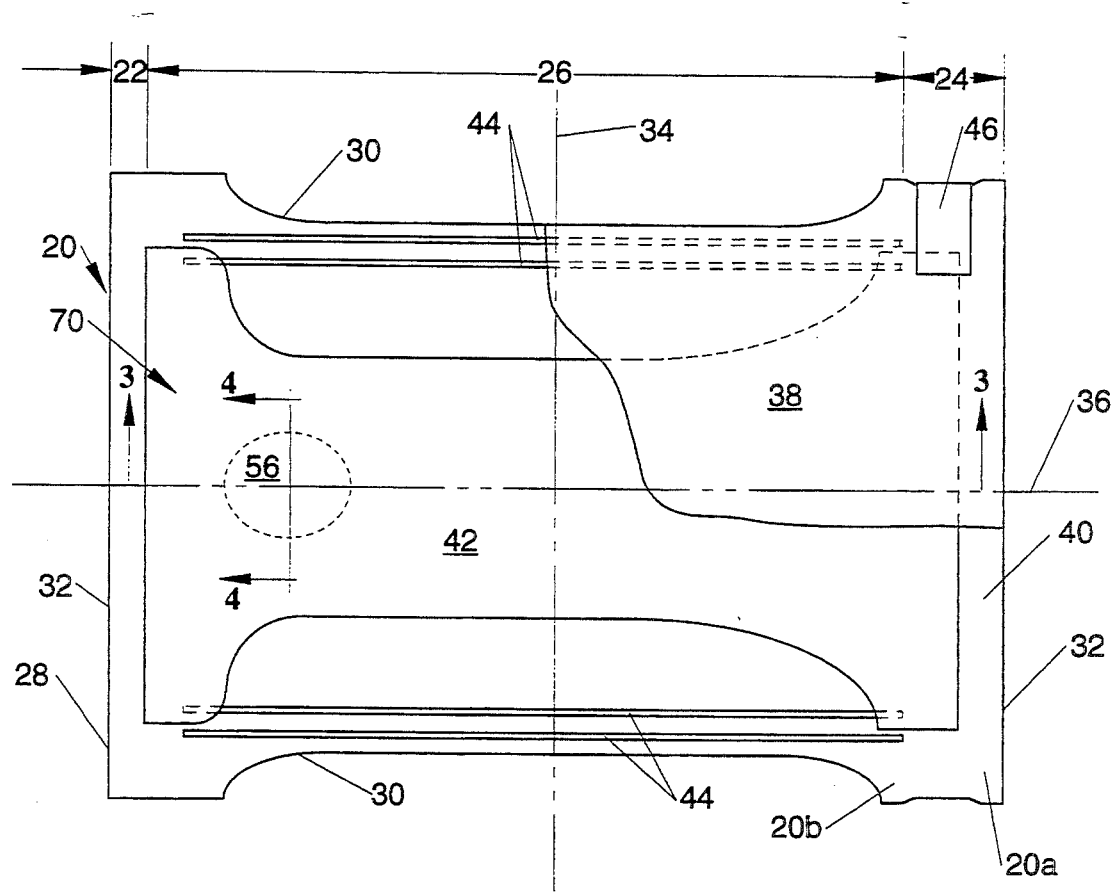
FIG. 2 is a plan view of a disposable diaper embodiment of the present invention wherein most of the topsheet has been cut-away to more clearly show the underlying absorbent core (an embodiment of an absorbent structure of the present invention) of the diaper.
Figure 3:
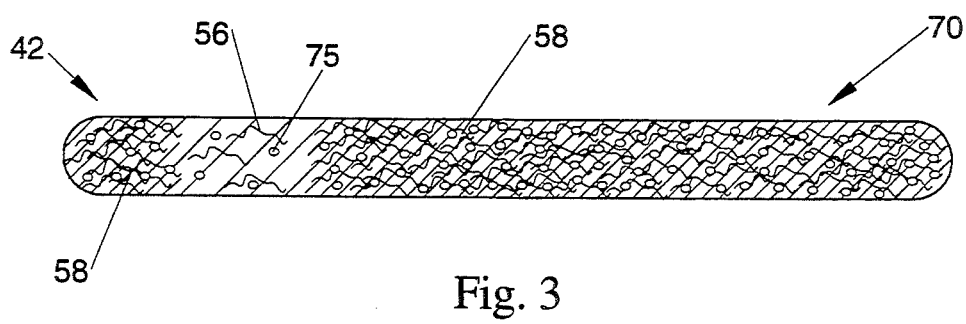
FIG. 3 is a longitudinal sectional view of only the absorbent core of the disposable diaper taken along sectional line 3—3 of FIG. 2.
Figure 4:
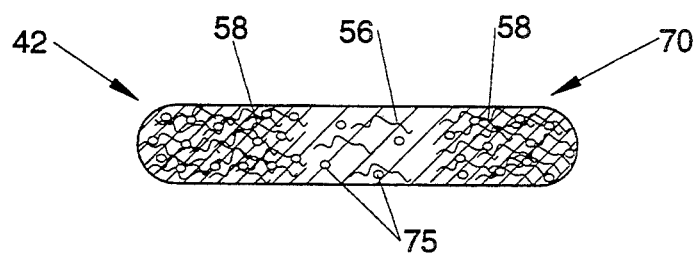
FIG. 4 is a transverse sectional view of only the absorbent core of the disposable diaper taken along sectional line 4—4 of FIG. 2.

A preferred embodiment of an absorbent article, diaper 20, is shown in FIG. 2. As used herein, the term "diaper" refers to a garment generally worn by infants and incontinent persons about the lower torso of the wearer. It should be understood, however, that the present invention is also applicable to other absorbent articles such as incontinent briefs, incontinent pads, training pants, diaper inserts, sanitary napkins, facial tissues, paper towels, and the like.

FIG. 2 is a plan view of the diaper 20 of the present invention in its flat-out, uncontracted state (i.e., with all the elastic induced contraction removed). Portions of the diaper have been cut-away to more clearly show the construction of the diaper 20. The body surface 20a of the diaper 20 (the portion of the diaper 20 which contacts the wearer) faces the viewer in FIG. 2. The diaper 20 is shown in FIG. 2 to have a front waistband region 22, a back waistband region 24, a crotch region 26, and a periphery 28. The periphery 28 is defined by the outer edges of the diaper 20. The longitudinal edges of the diaper 20 are designated 30 and the end edges are designated 32. The diaper 20 additionally has a transverse centerline which is designated 34 and a longitudinal centerline which is designated 36.

The diaper 20 preferably comprises a liquid pervious topsheet 38; a liquid impervious backsheet 40 joined with the topsheet 38; an absorbent core 42 (of which one or more absorbent structures 70 may form at least a part) positioned between the topsheet 38 and the backsheet 40; elastic members 44; and tape tab fasteners 46. The topsheet 38, the backsheet 40, the absorbent core 42, and the elastic members 44 may be assembled in a variety of well known configurations.

A preferred diaper configuration, however, is described generally in U.S. Pat. No. 3,860,003 entitled "Contractable Side Portions For Disposable Diaper", which issued to Kenneth B. Buell on Jan. 14, 1975. Alternatively preferred configurations for the disposable diapers contemplated herein are described in the following patents: U.S. Pat. No. 4,808,178 entitled "Disposable Absorbent Article Having Elasticized Flaps Provided With Leakage Resistant Portions" issued to Mohammed I. Aziz and Ted L. Blaney on Feb. 28, 1989; U.S. Pat. No. 4,695,278 entitled "Absorbent Article Having Dual Cuffs" issued to Michael I. Lawson on Sep. 22, 1987; and U.S. Pat. No. 4,816,025 entitled "Absorbent Article Having A Containment Pocket" issued to John H. Foreman on Mar. 28, 1989. The disclosures of all these patents are hereby incorporated by reference herein.

FIG. 2 shows a preferred embodiment of the diaper 20 in which the topsheet 38 and the backsheet 40 are co-extensive and have length and width dimensions generally larger than those of the absorbent core 42. The topsheet 38 is associated with and superimposed on the backsheet 40 thereby forming the periphery 28 of the diaper 20.

The front and back waistband regions 22 and 24, respectively of the diaper 20, extend from the end edges 32 of the diaper periphery 28 toward the transverse centerline 34 of the diaper 20. The front and back waistband regions 22 and 24 preferably extend a distance of about 5% of the length of the diaper 20. The waistband regions comprise the upper portions of the diaper 20, which, when worn, encircle the waist of the wearer. The crotch region 26 is that portion of the diaper 20 between the waistband regions 22 and 24. The crotch region 26 comprises the portion of the diaper 20 which, when worn, is positioned between the legs of the wearer and covers the lower torso of the wearer. The crotch region 26, thus, defines the area of typical liquid deposition for a diaper 20 or other disposable absorbent article.

The topsheet 38 is compliant, soft feeling, and non-irritating to the wearer's skin. Further, the topsheet 38 is liquid pervious permitting liquids to readily penetrate through its thickness. A suitable topsheet 38 may be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 38 is made of a hydrophobic material to isolate the wearer's skin from liquids in the absorbent core 42.

A particularly preferred topsheet 38 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which may be used to manufacture the topsheet 38. For example, the topsheet 38 may be woven, nonwoven, spunbonded, carded, or the like. A preferred topsheet is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction, and a wet tensile strength of at least about 55 grams per centimeter in the cross-machine direction.

The backsheet 40 is impervious to liquids and is preferably manufactured from a thin plastic film, although other flexible liquid impervious materials may also be used. As used herein, the term "flexible" refers to materials which are compliant and which will readily conform to the general shape and contours of the wearer's body. The backsheet 40 prevents the exudates absorbed and contained in the absorbent core 42 from wetting articles which contact the diaper 20 such as bedsheets and undergarments. Preferably, the backsheet 40 is polyethylene film having a thickness from about 0.012 mm (0.5 mil) to about 0.051 centimeters (2.0 mils).

A suitable polyethylene film is manufactured by Monsanto Chemical Corporation and marketed in the trade as Film No. 8020. The backsheet 40 is preferably embossed and/or matte finished to provide a more clothlike appearance. Further, the backsheet 40 may permit vapors to escape from the absorbent core 42 while still preventing exudates from passing through its thickness.

The size of the backsheet 40 is dictated by the size of the absorbent core 42 and the exact diaper design selected. In a preferred embodiment, the backsheet 40 has a modified hourglass-shape extending beyond the absorbent core 42 a minimum distance of at least about 1.3 centimeters to about 2.5 centimeters (about 0.5 to about 1.0 inch) around the entire diaper periphery 28.

The topsheet 38 and the backsheet 40 are joined together in any suitable manner. As used herein, the term "joined" encompasses configurations whereby the topsheet 38 is directly joined to the backsheet 40 by affixing the topsheet 38 directly to the backsheet 40, and configurations whereby the topsheet 38 is indirectly joined to the backsheet 40 by affixing the topsheet 38 to intermediate structures which in turn are affixed to the backsheet 40. In a preferred embodiment, the topsheet 38 and the backsheet 40 are affixed directly to each other in the diaper periphery 28 by attachment means such as an adhesive or any other attachment means as known in the art. Examples of such attachment means could include a uniform continuous layer of adhesive, a patterned layer of adhesive, or an array of separate lines or spots of adhesive.

The tape tab fasteners 46 are typically applied to the back waistband region 24 of the diaper 20 to provide a fastening means for holding the diaper 20 on the wearer. Only one of the tape tab fasteners is shown in FIG. 2. The tape tab fasteners 46 can be any of those well known in the art, such as the fastening tape disclosed in U.S. Pat. No. 3,848,594 issued to Kenneth B. Buell on Nov. 19, 1974, the disclosure of which patent is incorporated by reference herein. These tape tab fasteners 46 or other diaper fastening means are typically applied near the corners of the diaper 20.

The elastic members 44 are disposed adjacent the periphery 28 of the diaper 20, preferably along each longitudinal edge 30, so that the elastic members 44 will tend to draw and hold the diaper 20 against the legs of the wearer. Alternatively, the elastic members 44 may be disposed adjacent either or both of the end edges 32 of the diaper 20 to provide a waistband as well as (or rather than) leg cuffs. For example, a suitable waistband is disclosed in U.S. Pat. No. 4,515,595 entitled "Disposable Diapers With Elastically Contractible Waistbands" which issued to David J. Kievit and Thomas F. Osterhage on May 7, 1985, the disclosure of which patent is incorporated by reference herein. A method and apparatus suitable for manufacturing a disposable diaper having elastically contractible elastic members is described in U.S. Pat. No. 4,081,301 entitled "Method and Apparatus for Continuously Attaching Discrete, Stretched Elastic Strands to Predetermined Isolated Portions of Disposable Absorbent Products" which issued to Kenneth B. Buell on Mar. 28, 1978, the disclosure of which patent is incorporated by reference herein.

The elastic members 44 are secured to the diaper 20 in an elastically contractible condition so that in a normally unrestrained configuration, the elastic members 44 effectively contract or gather the diaper 20. The elastic members 44 can be secured in an elastically contractible condition in at least two ways. For instance, the elastic members 44 may be stretched and secured while the diaper 20 is in an uncontracted condition. Alternatively, the diaper 20 may be contracted, such as by pleating, and the elastic members 44 may be secured and connected to the diaper 20 while the elastic members 44 are in their relaxed or unstretched condition.

In the embodiment illustrated in FIG. 2, the elastic members 44 extend essentially the entire length of the crotch region 26 of the diaper 20. The elastic members 44 may, alternatively, extend the entire length of the diaper 20, or any other length suitable to provide an elastically contractible line. The length of the elastic members 44 is dictated by the diaper design.

The elastic members 44 may take a multitude of configurations. The width of the elastic members 44 may, for example, be varied from about 0.25 millimeters (0.01 inches) to about 25 millimeters (1.0 inch) or more. The elastic members 44 may comprise a single strand of elastic material or may comprise several parallel or non-parallel strands of elastic material. The elastic members 44 may be rectangular or curvilinear. Still further, the elastic members 44 may be affixed to the diaper in any of several ways which are known in the art. For example, the elastic members 44 may be ultrasonically bonded, heat and pressure sealed into the diaper 20 using a variety of bonding patterns, or simply be glued to the diaper 20.

The absorbent core 42 of the diaper 20 is positioned between the topsheet 38 and the backsheet 40. The absorbent core 42 may be manufactured in a wide variety of sizes and shapes (e.g., rectangular, hourglass, asymmetrical, etc.) and from a wide variety of materials. The total absorbent capacity of the absorbent core 42 should, however, be compatible with the design liquid loading for the intended use of the absorbent article or diaper. Further, the size and absorbent capacity of the absorbent core 42 may vary to accommodate wearers ranging from infants through adults. The absorbent core 42 preferably at least partially comprises some embodiment of the absorbent structure of the present invention (such as absorbent structure 70) which comprises a mixture of fiber material and specific amounts of particles of the superabsorbent hydrogel-forming material in the specific particle size distributions described herein.

A preferred embodiment of the diaper 20 has a modified hourglass-shaped absorbent core 42. The absorbent core 42 is preferably an absorbent structure 70 comprising a web or batt of airfelt, wood pulp fibers, and the particulate superabsorbent hydrogel-forming material disposed therein.

In other alternatives, the absorbent core 42 may comprise solely the particulate superabsorbent hydrogel-forming materials described herein; a combination of layers including the superabsorbent hydrogel-forming materials (including laminates as described herein); or, any other absorbent core configurations as are known in the art if the particulate superabsorbent hydrogel-forming materials described herein are incorporated into the same. Examples of such absorbent core configurations are described in U.S. Pat. Nos. 3,670,731 issued to Harmon on Jun. 20, 1972; 3,669,114 issued to Morane on Jun. 15, 1972; 3,888,257 issued to Cook et al. on Jun. 10, 1975; 3,901,236 issued to Assarsson et al. on Aug. 26, 1975; 4,102,340 issued to Mesek et al. on Jul. 25, 1978; and 4,500,315 issued to Pieniak et al. on Feb. 19, 1985. The disclosures of all these patents are incorporated by reference herein.

An exemplary embodiment of an absorbent core 42 that could be provided with the specific particle size distribution of superabsorbent hydrogel-forming material described above is the absorbent structure described in U.S. Pat. No. 4,610,678 entitled "High-Density Absorbent Structure" which issued to Paul T. Weisman and Stephen A. Goldman on Sep. 9, 1986. (Although the Weisman, et al. patent, like the following patents, is not directed to the specific invention described herein.) An alternative embodiment of an absorbent core 42 could be the dual-layered absorbent core having an asymmetric-shaped upper layer and a lower layer such as is generally described in U.S. Pat. No. 4,673,402 entitled "Absorbent Article With Dual-Layered Cores" which issued to Paul T. Weisman, Dawn I. Houghton, and Dale A. Gellert on Jun. 16, 1987. The disclosures of all of these patents are hereby incorporated by reference herein.

Figure 5:
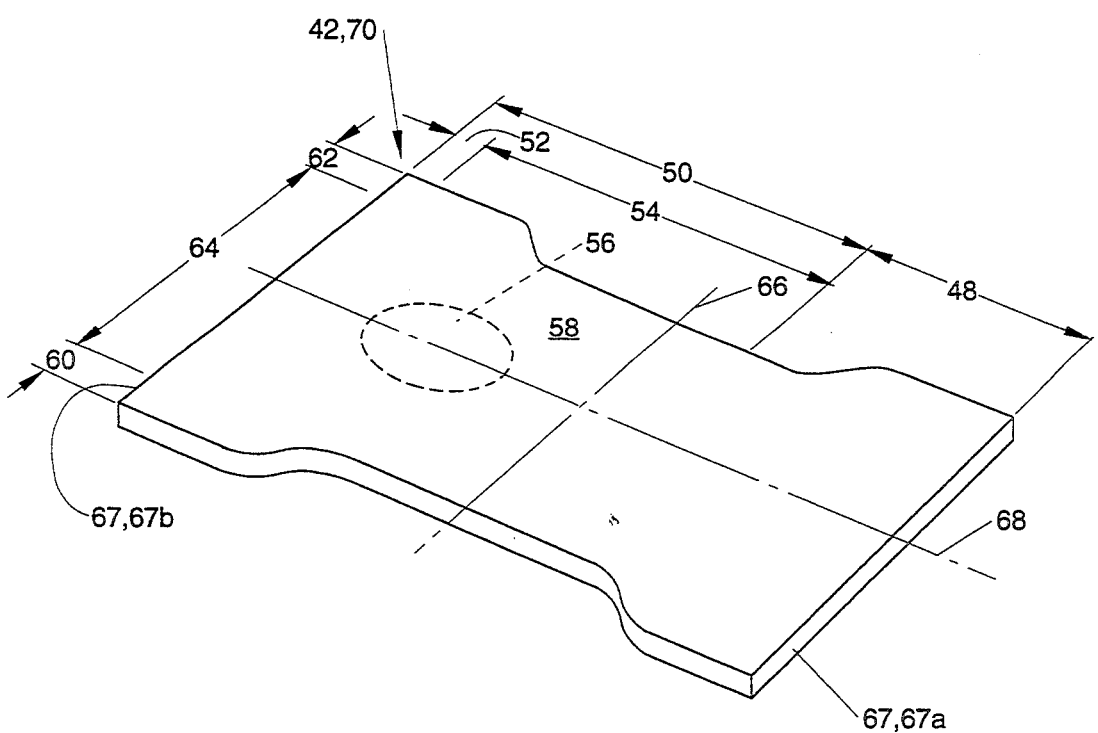
FIG. 5 is a perspective view of an absorbent structure of the present invention used as an absorbent core in the disposable diaper shown in FIG. 2.

A particularly preferred embodiment of the absorbent core 42 useful in the present invention is shown in FIG. 5. This embodiment, and the reference numbers shown in FIG. 5, are described in U.S. Pat. No. 4,834,735 entitled "High Density Absorbent Members Having Lower Density and Lower Basis Weight Acquisition Zones" issued to Miguel Alemany and Charles J. Berg on May 30, 1989. The Alemany, et al. patent discloses absorbent structures having a storage zone and an acquisition zone. The acquisition zone has a lower average density and a lower average basis weight per unit area than the storage zone so that the acquisition zone may effectively and efficiently rapidly acquire discharged liquids. The disclosure of this patent is also incorporated by reference herein.

The absorbent core 42 shown in FIG. 5 is preferably made by adding the particulate superabsorbent hydrogel-forming material to an air-entrained stream of fibers to affect uniform distribution of the superabsorbent hydrogel-forming material. The air-entrained stream of fibers is airlaid into a thickness profiled absorbent core-preform. The thickness profiled absorbent core initially has areas of higher basis weight which define the storage zone 58 and of lower basis weight which define the acquisition zone 56. The absorbent core-preform is calendering preferably to at least a uniform thickness in the deposition region in a fixed-gap calender roll to effect densifying of the absorbent core 42. This creates a lower average density and a lower average basis weight per unit area acquisition zone 56 relative to that of the storage Zone 58.

B. Some Alternative Embodiments

Figure 6:
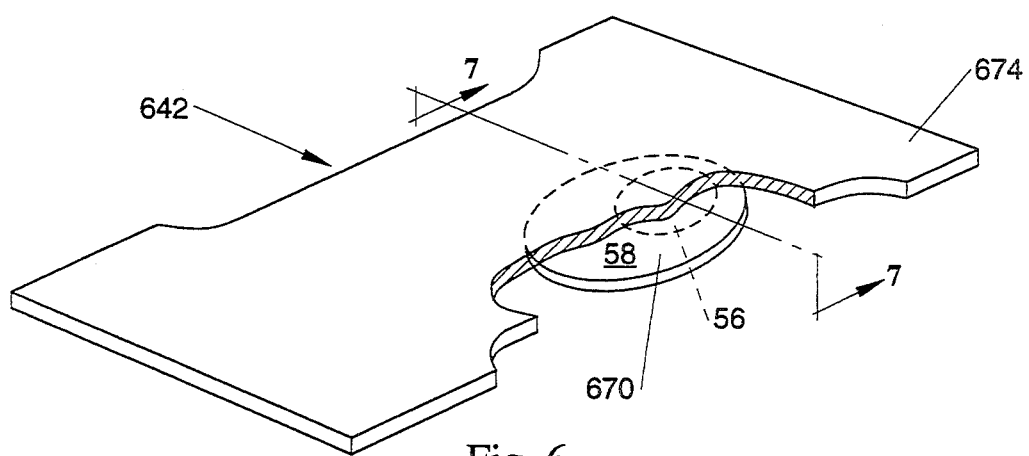
FIG. 6 is a perspective view of an alternative embodiment dual-layer absorbent core of the present invention.
Figure 7:
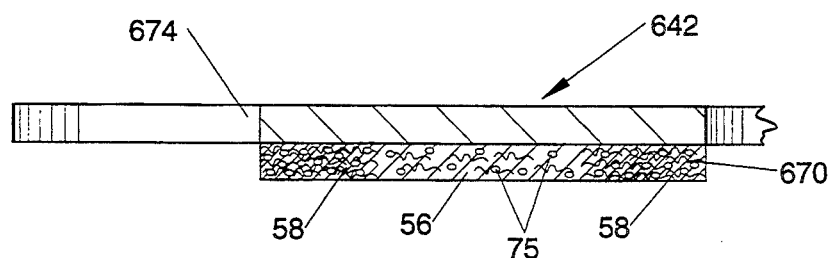
FIG. 7 is a sectional view of the dual-layer absorbent core of FIG. 6 taken along sectional line 7—7 of FIG. 6.

FIGS. 6 and 7 show a further alternative preferred embodiment of an absorbent core 642 of the present invention. In the embodiment shown in FIGS. 6 and 7, an absorbent acquisition layer 674 is positioned over an absorbent structure 670 to form a dual-layer absorbent core 642. The absorbent structure 670 is in the form of the absorbent core 42 described above with reference to FIGS. 2-5 (albeit in a different configuration). In a preferred embodiment, the absorbent article additionally comprises an absorbent acquisition layer juxtaposed on the absorbent core. The absorbent core preferably has a top surface area that is from about 0.25 to about 1.0 times that of the absorbent acquisition layer. In addition, the absorbent acquisition layer preferably has a top surface area that is from about 0.25 to about 1.0 times that of the absorbent article. An example of a dual-layer absorbent core (although not directed to the specific particle size distribution of superabsorbent hydrogel-forming material described herein) is discussed in more detail in the above-referenced U.S. Pat. No. 4,673,402, the disclosure of which is incorporated by reference herein.

Figure 8:
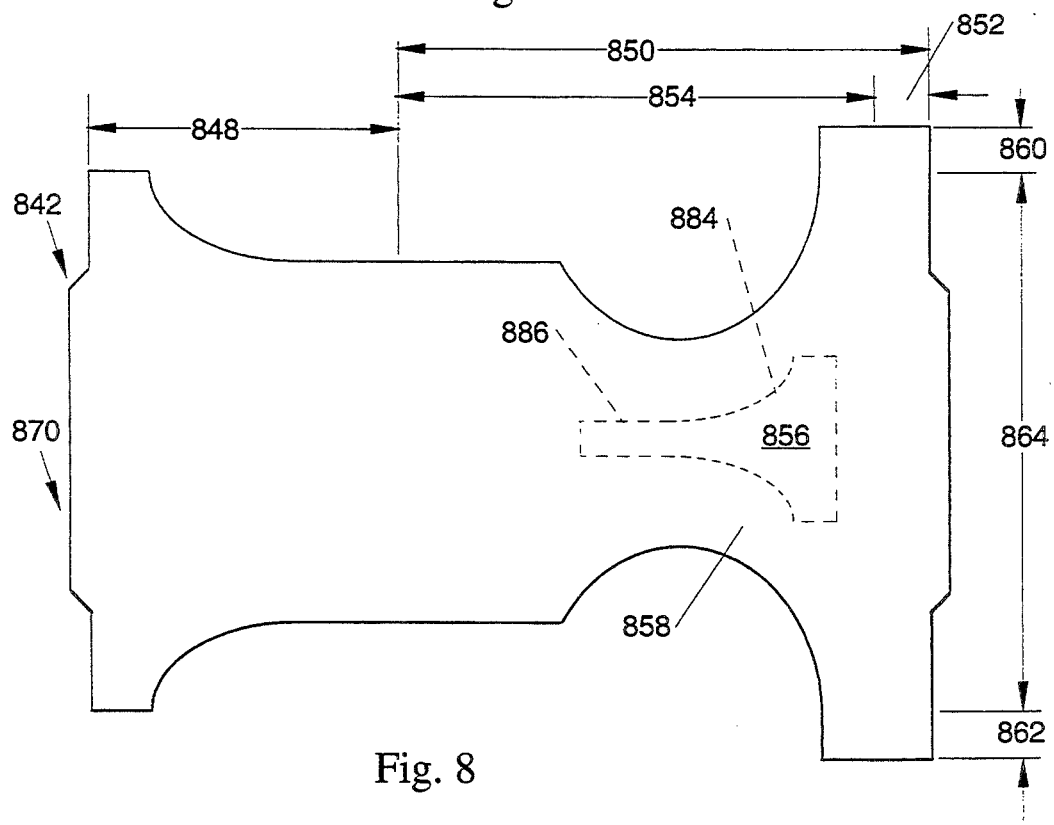
FIG. 8 is a plan view of a further alternative embodiment of an absorbent core of the present invention.

FIG. 8 shows a still further alternative embodiment of an absorbent core 842 comprising an absorbent structure 870 of the present invention. The absorbent core 842 has a modified hourglass shape that is asymmetric about its transverse centerline. The absorbent core 842 can be divided into regions that generally correspond to those of the absorbent core 42 shown in FIGS. 2-5. (These regions are described in greater detail in the aforementioned U.S. Pat. No. 4,834,735, the disclosure of which was incorporated by reference herein.) In the embodiment shown in FIG. 8, however, the density and basis weight of the ear regions 860 and 862 and the back section 848 are different from those of the storage zone 858 which is positioned in the central region 864.

In this embodiment, the cost of such absorbent core 842 is lowered because the extra material omitted from the ear regions and the back section provides no significant incremental benefits in leakage protection. (It should be understood that all or portions of the back section 848 and the ear regions 860 and 862 may alternatively be calendered to a lesser thickness than the central region 864 such that they have about an equal or a greater average density than the storage zone 858.) Further, although as shown in FIG. 8, the back section 848 preferably contains ears, it need not contain such ears.

Figure 9:
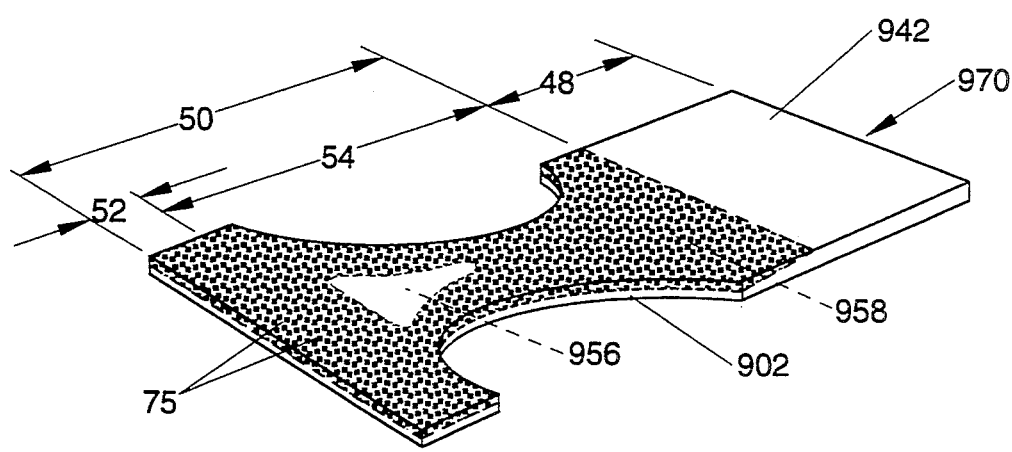
FIG. 9 is a perspective view of another alternative embodiment of an absorbent core of the present invention.

FIG. 9 shows a further alternative preferred embodiment of the present invention in which the absorbent core 942 comprises an absorbent structure 970 comprising a stratified matrix of fiber material and a mixture of fiber material and particles of the superabsorbent hydrogel-forming material 75. The absorbent core 942 comprises a storage zone 958, and an acquisition/distribution layer in the form of a dusting layer 902 such as that described in U.S. Pat. No. 4,888,231 entitled "Absorbent Core Having a Dusting Layer" issued to John Angstadt on Dec. 19, 1989, the disclosure of which is incorporated by reference herein. In this embodiment, a greater area of capillary gradients exists between the storage zone 958 and other portions of the absorbent core 942 so that the storage zone 958 and, more particularly, the particles 75 of the superabsorbent hydrogel-forming material are more efficiently used.

Figure 10:
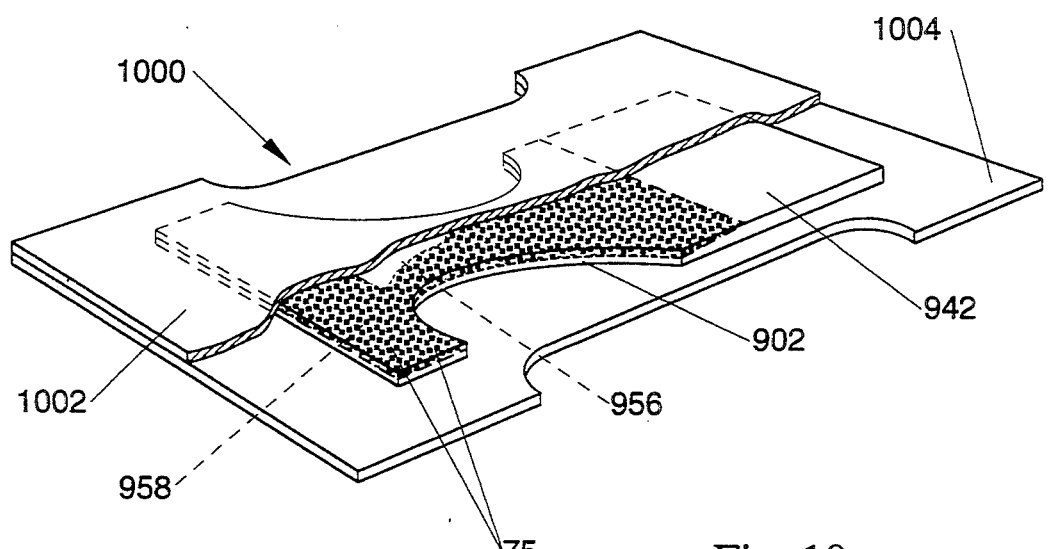
FIG. 10 is a cut-away perspective view of a disposable diaper embodiment of the present invention containing the absorbent core shown in FIG. 9.

FIG. 10 shows a perspective view of an alternative diaper embodiment of the present invention in which the absorbent core 942 of FIG. 9 is encased between a topsheet 1002 and a backsheet 1004 to form the disposable diaper 1000. The absorbent core 942 is preferably positioned such that the dusting layer 902 is positioned adjacent the backsheet 1004 so that the absorbent core 942 may function as described in U.S. Pat. No. 4,888,231.

Figure 11:
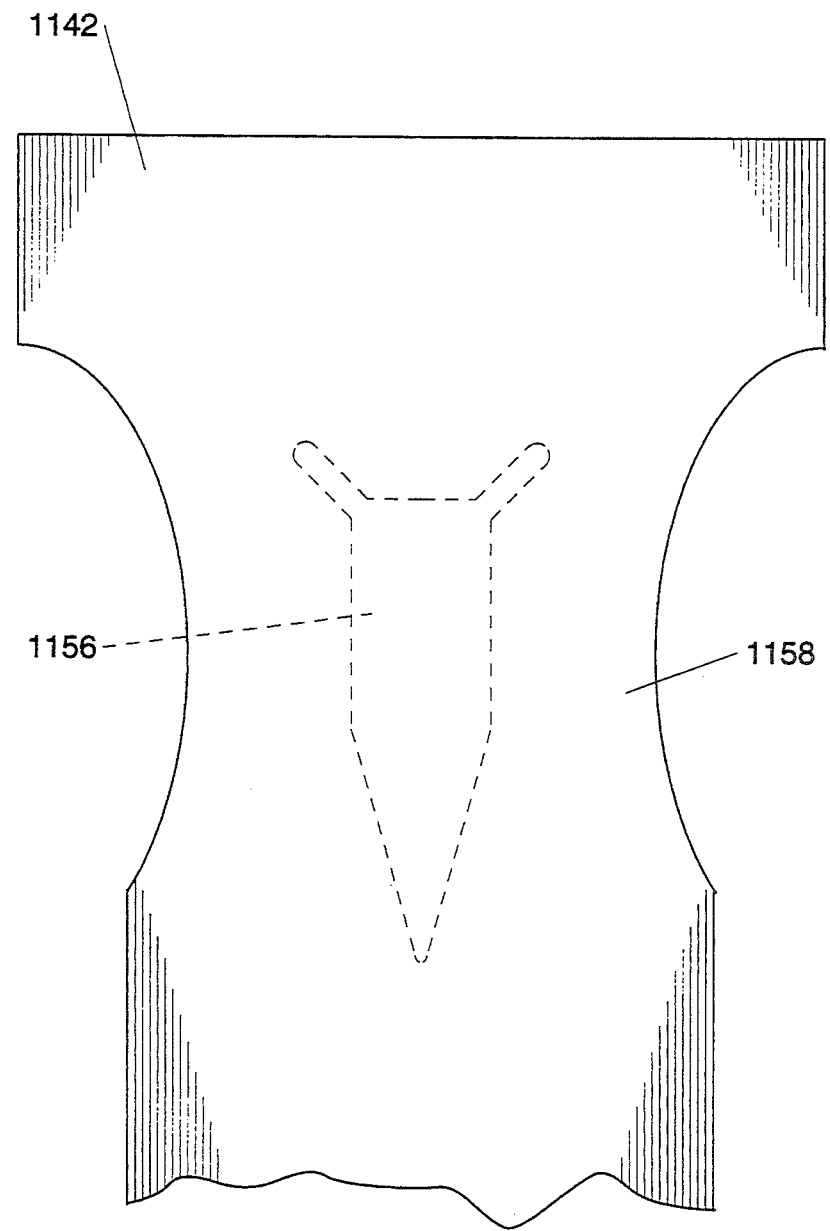
FIG. 11 is a top view of a portion of an absorbent core according to the present invention showing one embodiment of a shape for the acquisition zone.

FIG. 11 shows a further alternative embodiment of the present invention in which the acquisition zone 1156 (shown within the dotted lines) is "fox head-shaped." (So called because it resembles the front profile of a fox's head.) The fox head-shaped acquisition zone 1156 enhances fluid distribution for female wearers.

In other alternative to the embodiments described above, the pore size of the fibers in the absorbent cores may be varied without necessarily varying the density of the fibers to form an acquisition zone and a storage zone. For example, fine fiber dimensions of hardwood fluff can be utilized to advantage by substituting at least about 50%, and preferably about 80% to 100%, hardwood fluff fibers of approximately the same density as lower density softwood fluff fibers for the softwood fibers in the storage zone. This can be done because the hardwood fluff has a smaller pore size than the softwood fluff material. As result, a capillarity difference will still be obtained within the scope of the invention, even if the density of each zone is the same. Thus, for example, an absorbent core can be obtained from using a predominately softwood pulp with a fine pore structure to define the acquisition zone and a predominately hardwood fluff pulp to define the storage zone.

In use, the diaper 20 is applied to a wearer by positioning the back waistband region 24 under the wearer's back, and drawing the remainder of the diaper 20 between the wearer's legs so that the front waistband region 22 is positioned across the front of the wearer. The tape-tab fasteners 46 are then secured preferably to outwardly facing areas of the diaper 20.

TEST METHODS

The following procedures are conducted under standard laboratory conditions at 23° C. (73° F.) and 50% relative humidity.

A. Absorptive Capacity

The Absorptive Capacity of the superabsorbent hydrogel-forming material is determined by placing the superabsorbent hydrogel-forming material within a "tea bag", immersing the tea bag in an excess of Synthetic Urine for a specified period of time, and then centrifuging the tea bag for a specific period of time after it is removed from the Synthetic Urine. The ratio of superabsorbent hydrogel-forming material final weight after centrifuging minus initial weight (net fluid gain) to initial weight determines the Absorptive Capacity.

The tea bag material is cut using a 6 cm × 12 cm cutting die, folded in half lengthwise, and sealed along two sides with a T-bar sealer to produce a 6 cm × 6 cm square tea bag. The tea bag material utilized is a grade 1234 heat sealable material, obtainable from C. H. Dexter, Division of the Dexter Corp., Windsor Locks, Conn., U.S.A., or equivalent. Lower porosity tea bag material should be used if required to retain fine particles. After the tea bag is constructed, 0.200 grams, plus or minus 0.005 grams, of the superabsorbent hydrogel-forming material is weighed onto a weighing paper and transferred into the tea bag, and the top (open end) of the tea bag is sealed. An empty tea bag is sealed at the top and is used as a blank. Approximately 300 milliliters of Synthetic Urine are poured into a 1,000 milliliter beaker.

The specific synthetic urine used in the test methods of the present invention is referred to herein as "Synthetic Urine". The Synthetic Urine is commonly known as Jayco SynUrine and is available from Jayco Pharmaceuticals Company of Camp Hill, Pa. The formula for the Synthetic Urine is: 2.0 g/l of KCl; 2.0 g/l of $Na_2SO_4$; 0.85 g/l of $(NH_4)H_2PO_4$; 0.15 g/l $(NH_4)_2HPO_4$; 0.19 g/l of $CaCl_2$; and 0.23 g/l of $MgCl_2$. All of the chemicals are of reagent grade. The pH of the Synthetic Urine is in the range of 6.0 to 6.4.

The blank tea bag is submerged in the beaker containing Synthetic Urine. The tea bag containing the superabsorbent hydrogel-forming material (the sample tea bag) is held horizontally to distribute the material evenly throughout the tea bag. The sample tea bag is then laid on the surface of the Synthetic Urine. The sample tea bag is allowed to wet, for a period of no more than one minute, and then is fully submerged and soaked for 60 minutes.

Approximately two minutes after the first sample is submerged, a second set of tea bags, prepared identically to the first set of blank and sample tea bags, is submerged and soaked for 60 minutes in the same manner as the first set. After the prescribed soak time is elapsed for each set of tea bag samples, the tea bags are promptly removed (using tongs) from the Synthetic Urine. The samples are then centrifuged as described below.

The centrifuge used is a Delux Dynac II Centrifuge, Fisher Model No. 05-100-26, obtainable from Fisher Scientific Co. of Pittsburgh, Pa., or equivalent. The centrifuge should be equipped with a direct read tachometer and an electric brake. The centrifuge is further equipped with a cylindrical insert basket having an approximately 2.5 inch (6.35 cm) high outer wall with an 8.435 inch (21.425 cm) outer diameter, a 7.935 inch (20.155 cm) inside diameter, and 9 rows each of approximately 106 3/32 inch (0.238 cm) diameter circular holes equally spaced around the circumference of the outer wall, and having a basket floor with six ¼ inch (0.635 cm) diameter circular drainage holes equally spaced around the circumference of the basket floor at a distance of ½ inch (1.27 cm) from the interior surface of the outer wall to the center of the drainage holes, or an equivalent. The basket is mounted in the centrifuge so as to rotate, as well as brake, in unison with the centrifuge.

The sample tea bags are positioned in the centrifuge basket with a folded end of the tea bag in the direction of the centrifuge spin to absorb the initial force. The blank tea bags are placed to either side of the corresponding sample tea bags. The sample tea bag of the second set must be placed opposite the sample tea bag of the first set; and the blank tea bag of the second set opposite the blank tea bag of the first set, to balance the centrifuge. The centrifuge is started and allowed to ramp up quickly to a stable speed of 1,500 rpm. Once the centrifuge has been stabilized at 1,500 rpm, a timer is set for 3 minutes. After 3 minutes, the centrifuge is turned off and the brake is applied.

The first sample tea bag and the first blank tea bag are removed and weighed separately. The procedure is repeated for the second sample tea bag and the second blank tea bag.

The absorptive capacity (ac) for each of the samples is calculated as follows: ac=(sample tea bag weight after centrifuge minus blank tea bag weight after centrifuge minus dry superabsorbent hydrogel-forming material weight) divided by (dry superabsorbent hydrogel-forming material weight). The Absorptive Capacity value for use herein is the average absorptive capacity of the two samples.

B. Particle Size Determination by Sieve Analysis (the "Sieving Test")

The particle size of the superabsorbent hydrogel-forming material used in the absorbent structures of the present invention is determined by riffling a representative sample of particles of the superabsorbent material, then passing the sample through a set number of sieves of diminishing screen opening size.

The test procedure is as follows. One hundred grams of a representative sample of the superabsorbent hydrogel-forming material is riffled into between four and eight approximately equal fractions.

One of the fractions is then transferred onto a sieve stack. The sieves used in the test are all U.S. standard sieves. The stack should contain the screen sizes of interest to the experiment. For the analysis of the bulk particle size distribution in following Comparative Examples, the sieve stack contains, from the top, a standard #20 sieve (841 with micron openings), a standard #30 sieve (595 microns), a standard #50 sieve (297 microns), a standard #100 sieve (149 microns), a standard #325 sieve (44 microns), and a sieve pan.

For the analysis of the specific, more narrow particle size distributions in the following Examples (as well as the particle size distributions set forth in the appended claims), the sieve stack contains, from the top, a standard #50 sieve (297 microns), a standard #70 sieve (210 microns), a standard #100 sieve (149 microns), a standard #140 sieve (105 microns), a standard #170 sieve (88 microns), and a sieve pan.

Figure 17:
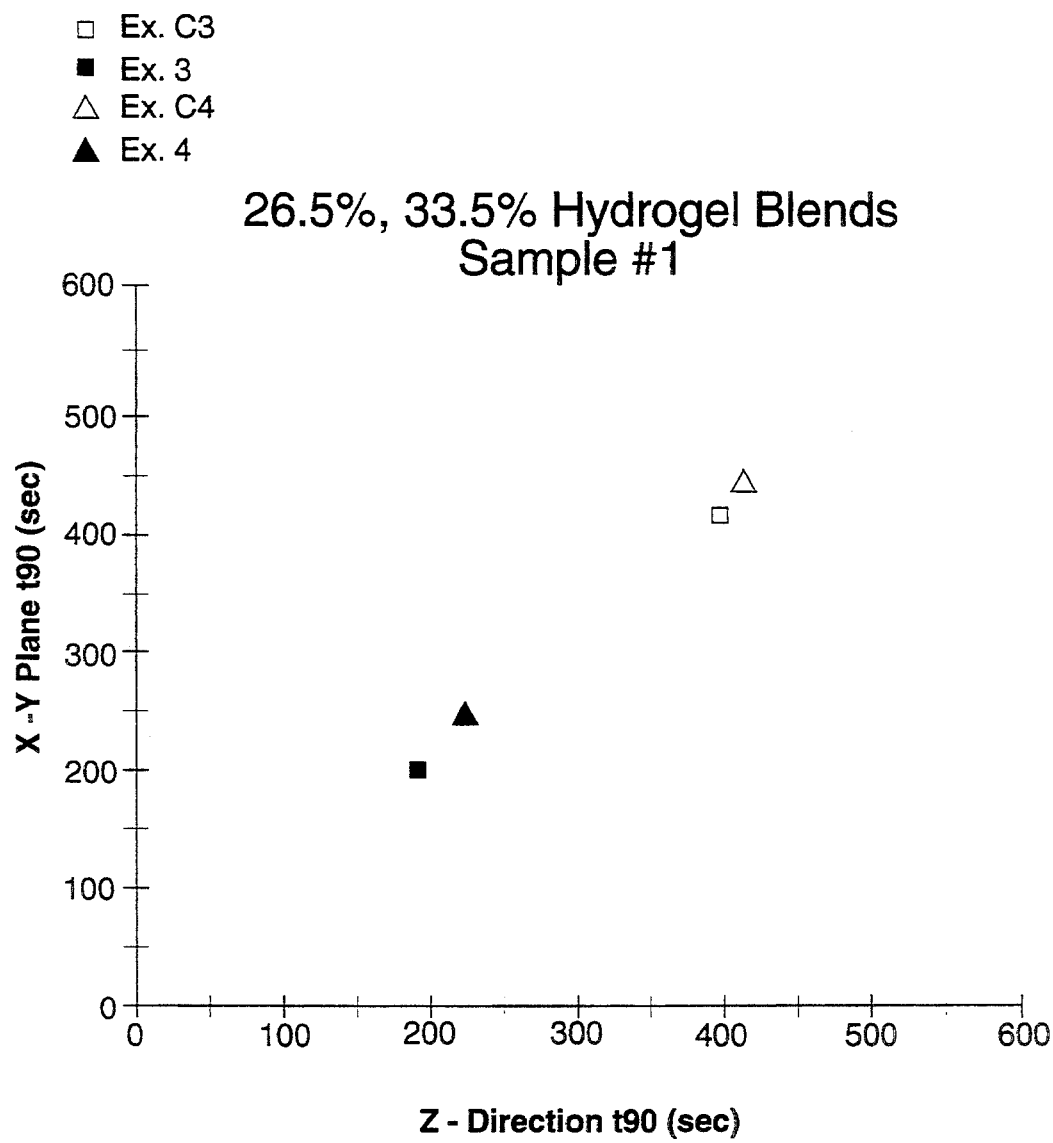
Figure 18:
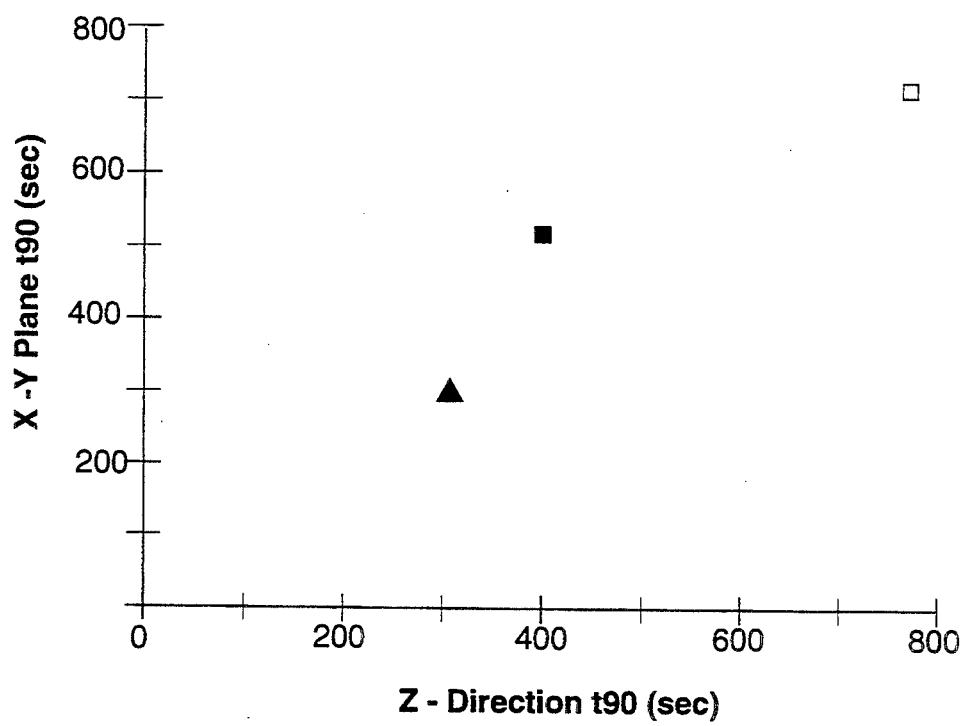
Figure 19:
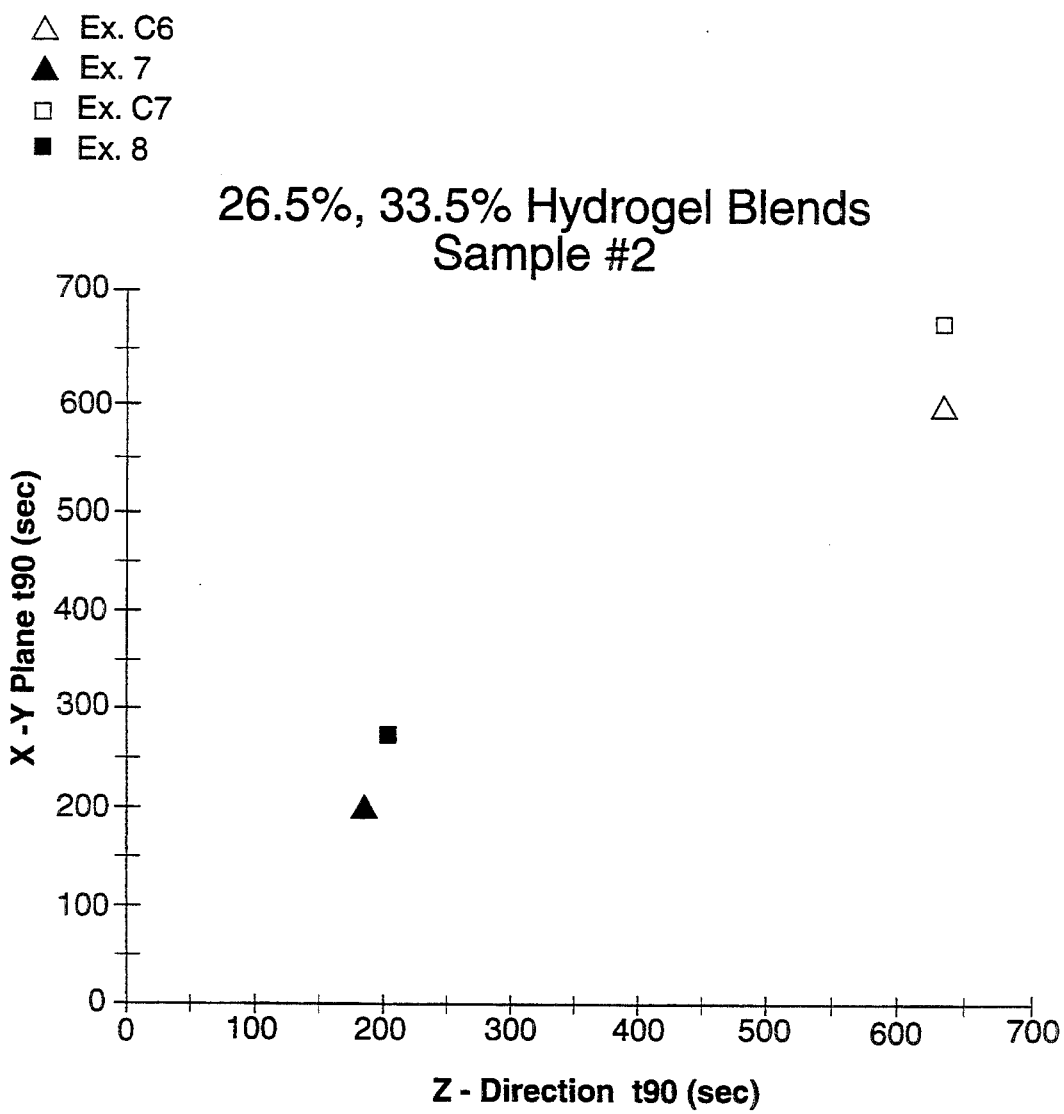
Figure 20:
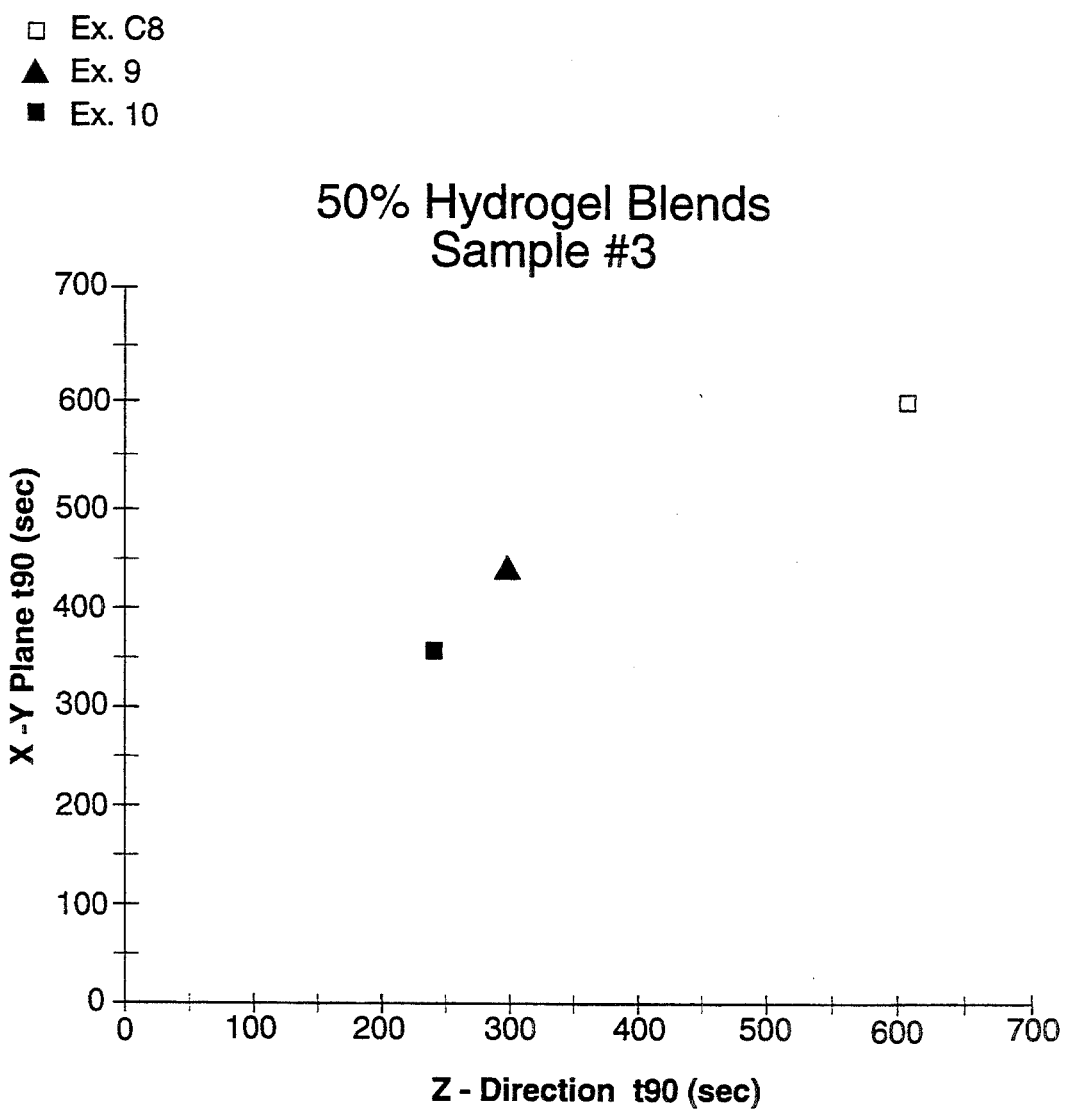

The riffled fraction of the superabsorbent material is sieved with a RO-TAP Testing Sieve Shaker Model SS-5, following the manufacturer's instructions. A RO-TAP sieve shaker is shown in FIG. 21-17 on page 21-19 of the reference publication *Perry's Chemical Engineers' Handbook, Sixth Edition,* (McGraw-Hill Book Company, 1984) previously incorporated by reference herein. The RO-TAP sieve shaker holds a series of sieves and rotates and taps the series of sieves with a mechanical motion similar to that used in sieving by hand. The tapping motion is applied by a hammer-like component to a "cork" in the center of the lid which covers the stack of sieves.

The sieve shaker, all sieves, and the sieve pan are obtainable from VWR Scientific of Chicago, Ill. The riffled fraction is shaken for 10 minutes under the following conditions. The sieve shaker should deliver between about 140–160 taps/minute. The sieve shaker should oscillate at a rate of approximately 270–300 revolutions per minute. The cork in the center of the sieve shaker lid should protrude exactly 3/16 inch (0.48 cm.).

The superabsorbent material retained on each sieve and the sieve pan after this process is weighed and recorded.

C. Demand Absorbency Test Method

This method consists of a version of a standard demand wettability test. For reference, standard demand absorbency tests are described in Chatterjee, P. K. (Ed.) *Absorbency,* Chapter II, pp. 60–62, Elsevier Science Publisher B. V., Amsterdam, The Netherlands (1985).

Figure 13:
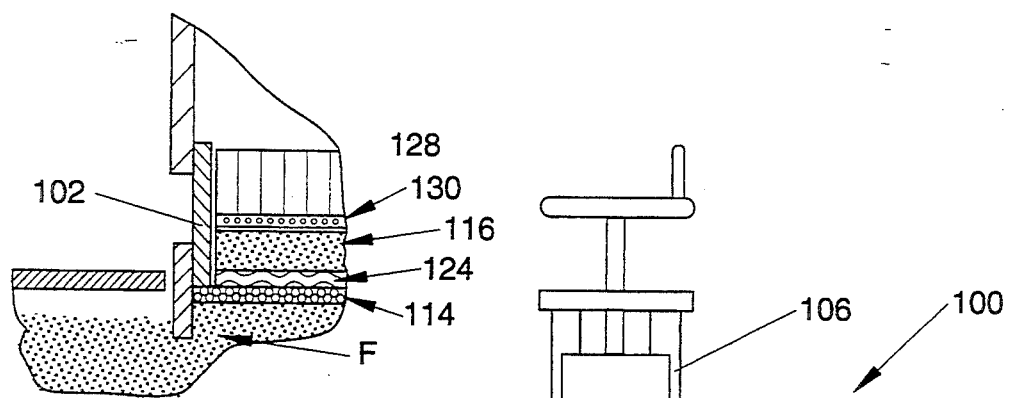
FIGS. 12 and 13 are schematic views of the apparatus used in the Demand Absorbency Test Method.
Figure 12:
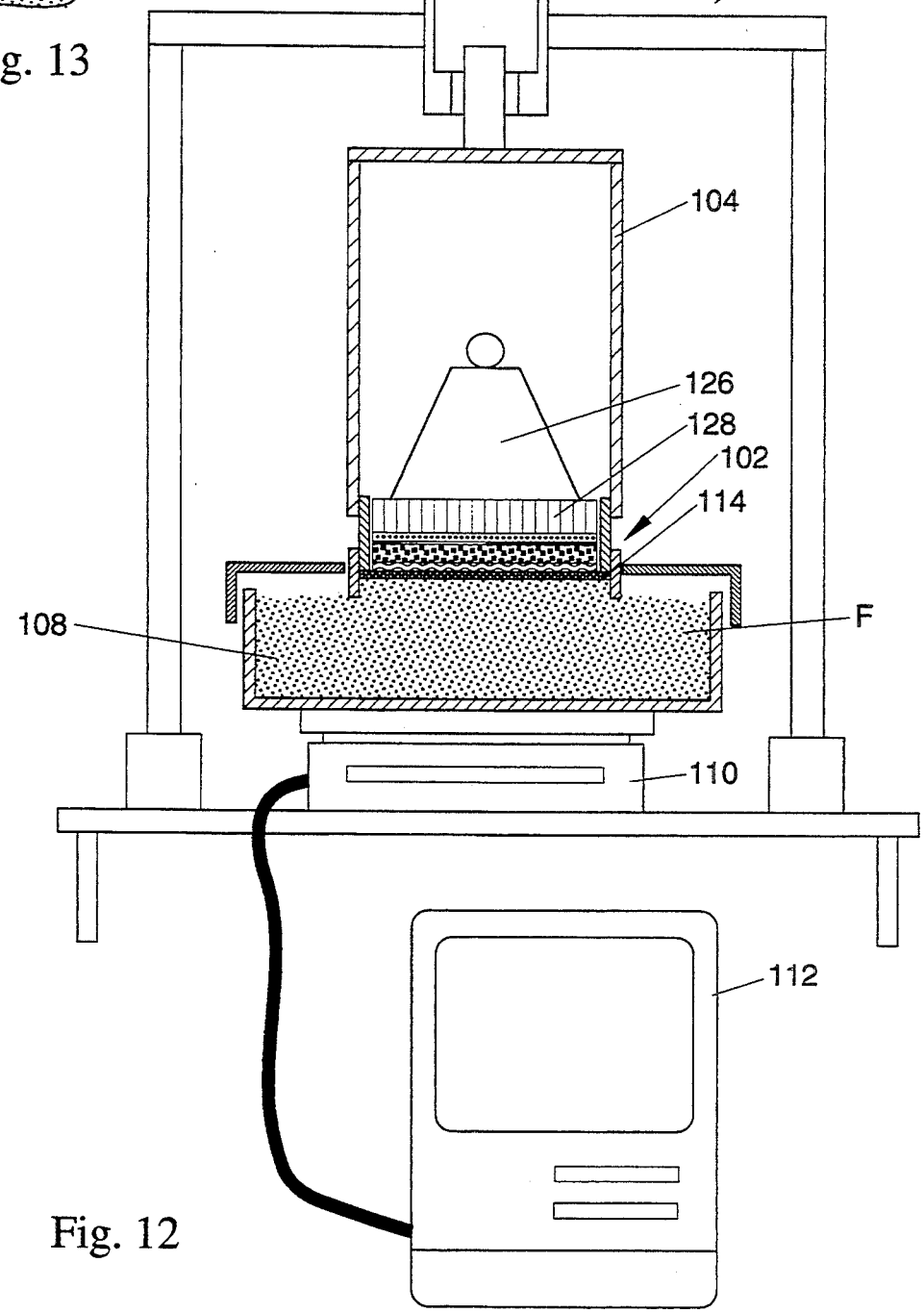

The apparatus used to conduct this test is shown schematically in FIGS. 12 and 13. The apparatus 100 consists of a square sample basket 102 suspended on a frame 104. The inside dimensions of the basket are 4"×4" (10.2 cm.×10.2 cm.). The height of the basket 102 is adjustable via a gear mechanism 106. A fluid reservoir 108 is placed on an electronic balance 110 directly under the sample basket 102. The balance 110 is connected to a computer 112.

There are two different types of sample baskets which may be used, depending on the version of the test being run. The two versions of the test are the z-direction version and the x-y plane version. The different versions of the test are used to measure the rate at which a sample of the absorbent core, or other absorbent structure, can absorb fluids that move through the sample in different directions, the z-direction and directions in the x-y plane.

The term "z-direction", as used herein, is an orientation with respect to the absorbent article 20 of the present invention if the absorbent article 20 is placed in a Cartesian coordinate system in its flat, laid out condition of FIG. 2 so that the garment surface 20b of the absorbent article 20 lies in the plane formed by the x and y axes (i.e., horizontal). The longitudinal and transverse centerlines (e.g., 36 and 34) of the absorbent article lie in the x-y plane. The "z-direction" is the direction that is perpendicular to the plane of either surface of the absorbent article 20 when it is in such a flat, laid out configuration.

Figure 14A:
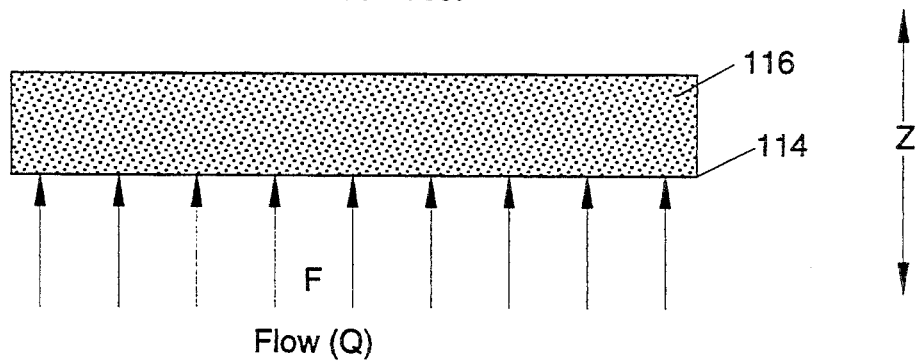
FIGS. 14A and B are an enlarged schematic representations of the different aspects of fluid processing that are of interest in the present invention.

The z-direction test is shown schematically in FIG. 14A. In the z-direction test, the entire 4"×4" bottom of the basket 102 consists of a coarse wire screen 114. The sample 116, therefore, contacts the fluid, F, as shown in FIG. 12. In this test, the sample 116 is only required to transport the fluid through the thickness of the sample in the vertical, or z-direction. This version of the test provides a measurement of the sample's potential fluid uptake rate.

Figure 14B:
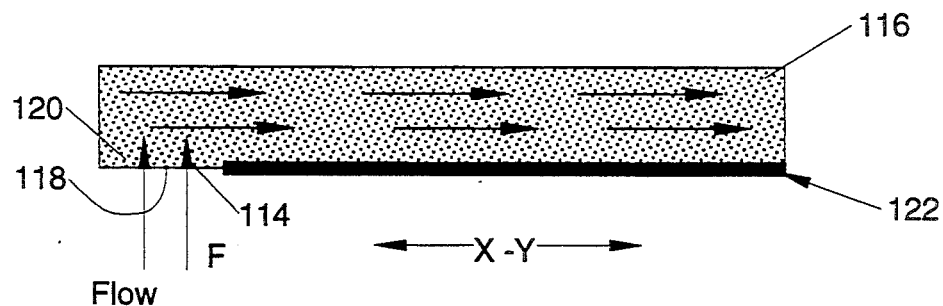

The x-y plane test is shown schematically in FIG. 14B. In the x-y plane test, the screen 114 is only present in a 1"×4" (2.54 cm.×10.2 cm.) area 118 along one edge 120 of the sample basket bottom. The remainder of the sample basket bottom, designated 122, is made of plexiglas and is fluid impervious. The sides of the sample basket that are in contact with the sample are also made of plexiglas and are fluid impervious (in the x-y plane test, and in the z-direction test). As shown in FIG. 14B, this test requires the sample 116 to first demand the fluid in the z-direction, and then transport it a maximum of 3 inches (7.62 cm.) in the horizontal (x-y) plane. The results from the x-y plane test provide a measurement of the sample's ability to distribute fluid under potential in-use conditions. Both the z-direction and x-y plane tests are done with the absorbent structure sample 116 confined under a 0.2 psi load applied evenly to the upper surface of the sample 116.

The test procedure is as follows. First, a 4"×4" (10.2 cm. ×10.2 cm.) sample of an absorbent structure is cut. The fluid reservoir 108 is filled with about 6800 ml of Synthetic Urine and set on an electronic balance 110 under the test apparatus 100. Then the sample basket 102 is lowered until the fluid level is just at the level near the top of the wire screen 114. A 4"×4" (z-direction) or 1"×4" (x-y plane), depending on the test being run, piece of commercially available 2-ply BOUNTY ® paper towel 124 is placed on the wire screen 114 in the bottom of the basket 102. The BOUNTY ® towel 124 ensures that consistent fluid contact with the underside of the core sample 116 is maintained throughout the duration of the test.

The applied weight 126 is attached to a square metal plate 128 with dimensions slightly smaller than the inner dimensions of the sample basket 102. Then the top side of the core sample 116 is attached to the bottom of the above-mentioned plate 128 via double sided tape 130, or spray adhesive. At time=zero, the sample 116 is placed into the sample basket 102 and the data acquisition program on the computer is activated. After 30 minutes, the test is stopped and the data analyzed and plotted.

One measurement of importance in analyzing the data is the sample's Synthetic Urine Capacity at 30 minutes. Other important properties of the sample are its the fluid uptake and distribution rates. The time it takes the sample to reach 90% of its 30 minute capacity provides a simple measure of the average fluid demand rate of the absorbent structure being tested. This is referred to as the t90 time and has units of seconds. A t90 time can be measured using both the z-direction test and the x-y plane test.

EXAMPLES

The following examples show the differences between t90 times for the z-direction and x-y plane tests for absorbent structures containing bulk particle size distributions of superabsorbent material and absorbent structures of the present invention which contain specific, relatively narrow, particle size distributions.

The absorbent structures for the examples provided below are produced using comminuted cellulose pulp and particulate hydrogel from various suppliers. The absorbent structures, in general, can be produced by the method and with the apparatus described in U.S. Pat. No. 4,610,678 issued to Weisman, et al., the disclosure of which is incorporated by reference.

For each example described below, the cellulose fibers and superabsorbent material in the desired weight percentages are mixed homogenously in an airstream and airlaid onto a moving belt to form an absorbent structure with the desired basis weight. The absorbent structures are then compressed to the desired density between driven roller nips. The densities specified in the examples are measured under an applied pressure of 0.1 psi. (about 7 g/cm$^2$).

The particle size distribution of the superabsorbent material for each example is important. Some Comparative Examples are made using bulk particle size distributions. The material used in both the absorbent structures containing bulk particle size distributions of superabsorbent material and in the absorbent structures containing the specific, relatively narrow, particle size distributions is obtained from three different commercial superabsorbent material suppliers (Samples 1, 2, and 3). The superabsorbent material supplied has the levels of extractable polymer material specified in U.S. Pat. No. Re. 32,649 issued to Brandt, et al. on Apr. 19, 1988. The bulk particle size distributions (determined from sieve analyses) for each of the samples tested are listed below.

TABLE 2

| BULK PARTICLE SIZE DISTRIBUTIONS | | | |
|---|---|---|---|
|  | Sample #1 | Sample #2 | Sample #3 |
| % on 20 mesh (841 microns) | 0.1 | 0.1 | 0.02 |
| % on 30 mesh (595 microns) | 9 | 19.4 | — |
| % on 50 mesh (297 microns) | 44 | 56.6 | 88.5 |
| % on 100 mesh (149 microns) | 30 | 16.0 | 10.0 |
| % on 325 mesh (44 microns) | 16 | 7.3 | 1.4 |
| % through 325 mesh | 1.6 | 0.7 | 0.02 |

The narrow particle size distributions of superabsorbent materials are produced by sieving the comparative bulk material. The material having the specific particle size distributions used in the absorbent structures is that which passes through the first sieve specified and is retained on the second sieve specified.

The Absorptive Capacities of some chosen samples of both the bulk particle size distributions as well as some of the preferred specific particle size distributions are set forth in the following table (Table 2A):

TABLE 2A

| ABSORPTIVE CAPACITIES | |
|---|---|
| Sample | Absorptive Capacity (g/g) |
| Sample #1 Bulk | 41.9 |
| Sample #1 50/100 mesh | 41.6 |
| Sample #2 Bulk | 39.9 |
| Sample #2 50/100 mesh | 40.0 |
| Sample #3 Bulk | 41.1 |
| Sample #3 50/100 | 42.1 |

The other specific conditions for each of the Examples are described in more detail in Table 3. The results of z-direction and x-y plane demand absorbency tests conducted on each example absorbent structure are set forth in Table 4. (In Tables 3 and 4, an example designated by the letter C is referred to as a Comparative Example. The Comparative Examples generally comprise those with bulk particle size superabsorbent materials or with superabsorbent material particle sizes that are outside of the specific particle size ranges used in the absorbent structures of the present invention.)

TABLE 3

| ABSORBENT STRUCTURE DATA | | | | | |
|---|---|---|---|---|---|
| EXAMPLE | HYDROGEL TYPE | MESH SIZE FRACTION | HYDROGEL WEIGHT % | BASIS WT. (g/in$^2$) | DENSITY (g/cm$^3$) |
| C$^1$ | Sample #1 | Bulk psd* | 50 | 0.29 | 0.17 |
| 1 | Sample #1 | 50/100 | 50 | 0.29 | 0.23 |
| 2 | Sample #1 | 50/70 | 50 | 0.29 | 0.23 |
| C$^2$ | Sample #1 | 100/170 | 50 | 0.28 | 0.37 |
| C$^3$ | Sample #1 | Bulk psd | 26.5 | 0.58 | 0.086 |
| 3 | Sample #1 | 50/100 | 26.5 | 0.61 | 0.087 |
| C$^4$ | Sample #1 | Bulk psd | 33.5 | 0.63 | 0.092 |
| 4 | Sample #1 | 50/100 | 33.5 | 0.69 | 0.098 |
| C$^5$ | Sample #2 | Bulk psd | 50 | 0.27 | 0.21 |

TABLE 3-continued

ABSORBENT STRUCTURE DATA

| EXAMPLE | HYDROGEL TYPE | MESH SIZE FRACTION | HYDROGEL WEIGHT % | BASIS WT. (g/in$^2$) | DENSITY (g/cm$^3$) |
|---|---|---|---|---|---|
| 5 | Sample #2 | 50/100 | 50 | 0.27 | 0.20 |
| 6 | Sample #2 | 40/120 | 50 | 0.25 | 0.18 |
| C$^6$ | Sample #2 | Bulk psd | 26.5 | 0.61 | 0.083 |
| 7 | Sample #2 | 50/100 | 26.5 | 0.60 | 0.081 |
| C$^7$ | Sample #2 | Bulk psd | 33.5 | 0.67 | 0.09 |
| 8 | Sample #2 | 50/100 | 33.5 | 0.62 | 0.078 |
| C$^8$ | Sample #3 | Bulk psd | 50 | 0.26 | 0.17 |
| 9 | Sample #3 | 50/100 | 50 | 0.25 | 0.19 |
| 10 | Sample #3 | 50/120 | 50 | 0.27 | 0.18 |

*"psd" is particle size distribution.

TABLE 4

DEMAND ABSORBENCY DATA

| | FLUID UPTAKE (Z-DIRECTION) | | FLUID DISTRIBUTION (X-Y PLANE) | |
|---|---|---|---|---|
| EXAMPLE | t90 (sec) | 30 Minute Capacity (g/g) | t90 (sec) | 30 Minute Capacity (g/g) |
| C$^1$ | 575 | 22.1 | 480 | 22.8 |
| 1 | 260 | 26.4 | 350 | 25.9 |
| 2 | 290 | 24.2 | 410 | 24.5 |
| C$^2$ | 80 | 21.2 | 980 | 23.8 |
| C$^3$ | 390 | 13.6 | 410 | 15.2 |
| 3 | 180 | 14.3 | 205 | 15.8 |
| C$^4$ | 405 | 14.2 | 445 | 15.5 |
| 4 | 220 | 15.8 | 270 | 17.5 |
| C$^5$ | 770 | 19.3 | 700 | 24.5 |
| 5 | 330 | 18.9 | 305 | 23.0 |
| 6 | 400 | 22.3 | 520 | 22.8 |
| C$^6$ | 620 | 14.4 | 600 | 15.2 |
| 7 | 180 | 14.5 | 205 | 14.6 |
| C$^7$ | 625 | 17.1 | 665 | 16.6 |
| 8 | 205 | 15.9 | 265 | 15.7 |
| C$^8$ | 620 | 20.4 | 590 | 23.1 |
| 9 | 290 | 21.3 | 445 | 23.6 |
| 10 | 245 | 20.2 | 355 | 22.9 |

Figure 15:
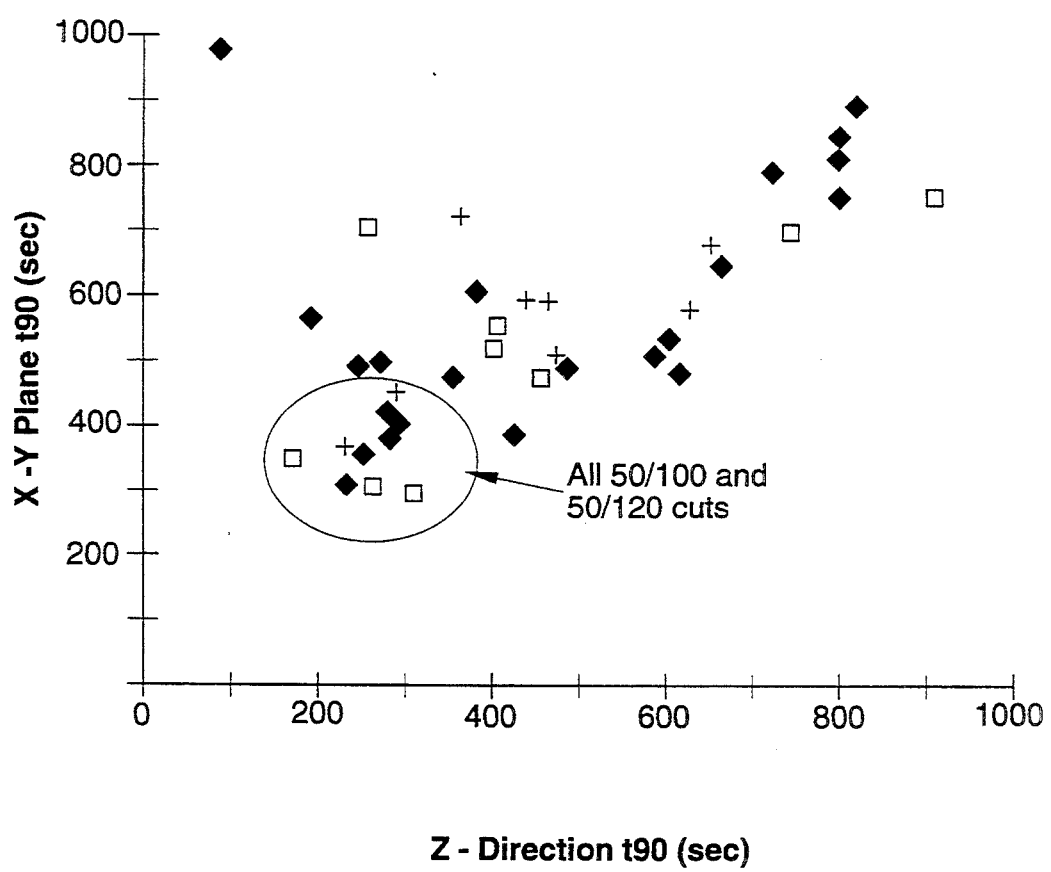
FIG. 15 is a graphical representation which depicts the fluid processing characteristics of various particle size distributions of superabsorbent materials in cellulose fiber structures containing 50% by weight superabsorbent material and 50% by weight cellulose fibers.

The results of the z-direction and x-y plane tests for the foregoing Examples and Comparative Examples which contain 50% by weight cellulose fibers and 50% by weight superabsorbent material can be summarized in the graph shown as FIG. 15. (It should be understood that FIG. 15 shows not only the data provided in Table 4 for the 50% blends, but data associated with absorbent structures having various other particle size distributions in 50% blends.)

The x-axis of the graph represents the time in seconds it takes for the sample tested to reach 90% of its z-direction test capacity. The y-axis of the graph represents the time in seconds it takes for the sample to reach 90% of its x-y plane test capacity.

The particle size distributions in the upper right hand corner of the graph represent those of relatively wide distributions of particle sizes, which usually contain relatively large particles that are typically received from manufacturers. The graph shows that webs containing these particles take a relatively long time to reach both their z-direction capacity and x-y plane capacity.

The particle size distributions in the upper left hand corner of the graph represent those of relatively fine particles. The graph shows that while webs containing fine particles take in fluids quickly in the z-direction, they are relatively slow to reach capacity in the x-y plane. This is a result of the problem of gel blocking described previously.

The ideal particle size distributions are those in the lower left hand corner of the graph. These are the webs containing particle sizes which are the quickest to reach their z-direction capacity and x-y plane capacity. These particle size distributions are representative of the specific narrow particle size distributions of superabsorbent hydrogel-forming materials used in the present invention.

The absorbent structures of the present invention are those at least a portion of which typically have t90 z-direction and x-y plane demand absorbency times (or rates) of less than or equal to about 500 seconds when the absorbent structure is tested according to the Demand Absorbency Test (for both z-direction and x-y plane tests). In the Demand Absorbency Test, the portion of the core tested is selected in accordance with the criteria set forth in the Weight Percentage Analysis, except that the size of the sample portion is the standard 4"×4" (10.2 cm.×10.2 cm.) sample, rather than a 25 square centimeter portion.

Preferably, the absorbent structures described herein have t90 z-direction and x-y plane demand absorbency times (or rates) of less than or equal to about 500 seconds, preferably less than or equal to about 400 seconds, more preferably less than or equal to about 300 seconds, and most preferably less than or equal to about 225 seconds for each test.

As shown in the attached graphs, the demand absorbency times are roughly related to the superabsorbent material concentrations used in the absorbent structures. For instance, the absorbent structures with the latter three t90 times specified above (i.e., 400, 300, and 225 seconds) generally have superabsorbent material concentrations of about 50%, 35%, and 25%, respectively.

FIGS. 16 through 20 depict the data for absorbent structures in Table 4, in graphical form. Each of these figures shows the data for an absorbent structure containing specific concentrations of superabsorbent material provided by one of the different superabsorbent material suppliers. The figures each show the results for the z-direction and x-y plane tests for absorbent structures containing superabsorbent material in either bulk form or another form which is outside the range of particle sizes used in the absorbent structures of the present invention, and the results for the absorbent structures of the present invention.

These figures clearly show that the absorbent structures containing high concentrations of superabsorbent hydrogel-forming particles in the narrow particle size distributions described herein (Examples 1–10) have faster z-direction and x-y plane fluid demand rates than absorbent structures containing bulk particle size distributions (Examples C$^1$, C$^3$–C$^8$). This is the case for absorbent structures containing various concentrations of the superabsorbent hydrogel-forming material (for example, 26.5%, 33.5%, and 50%).

Figure 16:
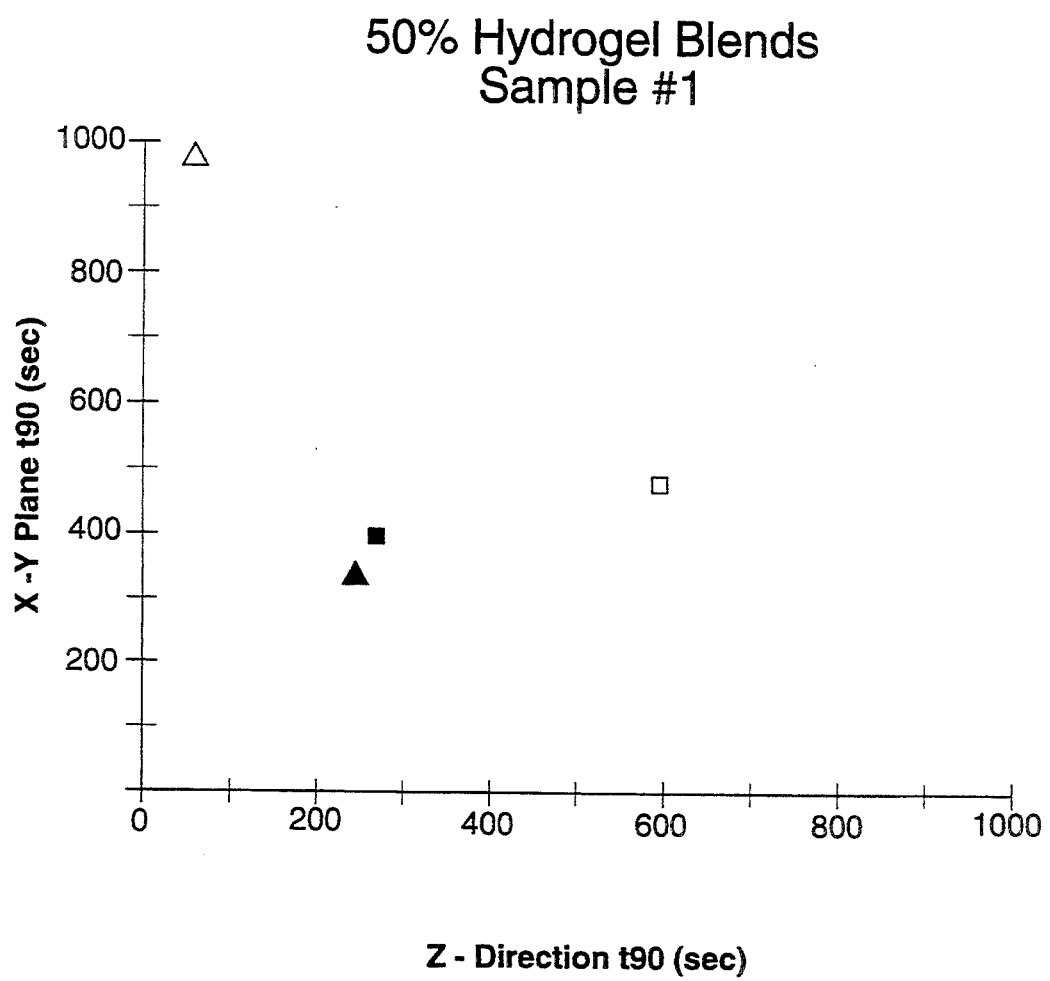
FIGS. 16 through 20 depict the data in Table 4 in graphical form.

FIG. 16 also provides a comparison of the absorptive rates of structures containing very fine particles of superabsorbent hydrogel-forming material with the absorbent structures of the present invention. Example $C^2$ contains superabsorbent particles in a 100/170 mesh fraction (fine sized particles). FIG. 16 shows that while this sample is faster than Examples 1 and 2 in the z-direction test, it is significantly slower in the x-y plane. This is believed to be due to the gel-blocking phenomena associated with the fine particles.

In addition, as shown in Table 4, the increase in fluid processing rates associated with the use of the narrow particle size distributions does not result in any decrease in 30 minute absorptive capacity for the absorbent structures of the present invention.

The present invention, thus, provides absorbent structures that are capable of quickly taking in, distributing, and storing fluids. It is believed that the problems encountered in many earlier absorbent structures are substantially reduced or eliminated in the absorbent structures of the present invention. The absorbent structures contain reduced amounts of the relatively large particles which take in fluids relatively slowly, as well as reduced amounts of relatively fine particles that have a tendency to gel block and slow down the transmission of fluids in the x-y plane. The absorbent structures of the present invention are believed to have improved containment performance (and, thus, reduced tendency to leak) because they are capable of quickly processing fluids that are deposited upon them.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent structure comprising a primary structure and a plurality of particles of substantially water-insoluble, absorbent, hydrogel-forming, polymer material in said primary structure, said particles of polymer material being formed by solution polymerization methods and distributed in a concentration of between about 35% and about 90% by weight of said absorbent structure in at least a 25 square centimeter portion of said absorbent structure according to the Weight Percentage Analysis, which particles are of such size that at least about 85% of said particles, by weight, will pass through a U.S. Standard 50 mesh sieve with 297 micron openings and be retained on a U.S. Standard 140 mesh sieve with 105 micron openings when said particles are tested according to the Sieving Test.

2. The absorbent structure of claim 1 wherein at least about 90% of said particles by weight, will pass through a U.S. Standard 50 mesh sieve with 297 micron openings and be retained on a U.S. Standard 140 mesh sieve with 105 micron openings when said particles are tested according to the Sieving Test.

3. The absorbent structure of claim 2 wherein at least about 95% of said particles by weight, will pass through a U.S. Standard 50 mesh sieve with 297 micron openings and be retained on a U.S. Standard 140 mesh sieve with 105 micron openings when said particles are tested according to the Sieving Test.

4. The absorbent structure of claim 1 wherein said primary structure at least partially comprises a fiber material, and said polymer material is mixed with said fiber material.

5. The absorbent structure of claim 4 wherein said fiber material is hydrophilic.

6. The absorbent structure of claim 4 wherein said fiber material comprises wood pulp fibers.

7. The absorbent structure of claim 1 wherein said particles are uniformly distributed throughout the absorbent structure.

8. The absorbent structure of claim 1 wherein said particles are distributed in a positive gradient through at least a portion of the thickness of the absorbent structure.

9. The absorbent structure of claim 1 wherein said primary structure comprises two or more webs of nonwoven material and said particles are disposed between said nonwoven webs.

10. The absorbent structure of claim 4 having an overall fiber/polymer material composition weight ratio of from about 90:10 to about 2:98.

11. The absorbent structure of claim 10 having an overall fiber/polymer material composition weight ratio of from about 75:25 to about 2:98.

12. The absorbent structure of claim 1 wherein said polymer material comprises network crosslinked products of partially neutralized polyacrylic acid.

13. The absorbent structure of claim 1 wherein said polymer material is selected from the group consisting of hydrolyzed starch-acrylonitrile graft copolymers, partially neutralized starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile copolymers, hydrolyzed acrylamide copolymers, network crosslinked products of any of the foregoing copolymers, and partially neutralized polyacrylic acid.

14. The absorbent structure of claims 1, 12, or 13 wherein at least some of said polymer material particles are surface crosslinked.

15. An absorbent structure comprising a primary structure and a plurality of particles of substantially water-insoluble, absorbent, hydrogel-forming, polymer material in said primary structure, said particles of polymer material being formed by solution polymerization methods and distributed in a concentration of between about 35% and about 90% by weight of said absorbent structure in at least a 25 square centimeter portion of said absorbent structure according to the Weight Percentage Analysis, which particles are of such size that at least about 85% of said particles, by weight, will pass through a U.S. Standard 50 mesh sieve with 297 micron openings and be retained on a U.S. Standard 140 mesh sieve with 105 micron openings when said particles are tested according to the Sieving Test, wherein said portion having particles of polymer material distributed in a concentration of between about 35% and about 90% by weight of said absorbent structure has t90 z-direction and x-y plane demand absorbency rates of less than or equal to about 500 seconds when said portion is tested according to the Demand Absorbency Test.

16. The absorbent structure of claim 15 wherein said portion has t90 z-direction and x-y plane demand absorbency rates of less than or equal to about 300 seconds when said portion is tested according to the Demand Absorbency Test.

17. The absorbent structure of claim 16 wherein said portion has t90 z-direction and x-y plane demand absorbency rates of less than or equal to about 225 seconds when said portion is tested according to the Demand Absorbency Test.

18. An absorbent article comprising:
a liquid pervious topsheet;
a liquid impervious backsheet joined to said topsheet; and an absorbent core positioned between said topsheet and said backsheet, said absorbent core comprising a primary structure and a plurality of particles of substantially water insoluble, absorbent, hydrogel-forming, polymer material in said primary structure, said particles of polymer material being formed by solution polymerization methods and distributed in a concentration of between about 35% and about 90% by weight of said absorbent core in at least a 25 square centimeter portion of said absorbent core according to the Weight Percentage Analysis, which particles are of such size that at least about 85% of said particles, by weight, will pass through a U.S. Standard 50 mesh sieve with 297 micron openings and be retained on a U.S. Standard 140 mesh sieve with 105 micron openings when said particles are tested according to the Sieving Test.

19. The absorbent article of claim 18 wherein said absorbent core additionally comprises an acquisition zone, said acquisition zone having a perimeter and a lateral area, and a storage zone at least partially laterally surrounding the perimeter of said acquisition zone so as to be in liquid communication with at least a portion of the lateral area of said acquisition zone, said acquisition zone having a lower average density and a lower average basis weight per unit area than said storage zone.

20. The absorbent article of claim 18 wherein said absorbent core has a body-facing side and a garment-facing side, and additionally comprises an absorbent acquisition layer juxtaposed on the body-facing side of said absorbent core.

21. The absorbent article of claim 18 additionally comprising a dusting layer consisting essentially of hydrophilic fiber material positioned subjacent the absorbent core, next to the backsheet.

22. The absorbent article of claim 18 wherein at least about 90% of said particles by weight in said absorbent core will pass through a U.S. Standard 50 mesh sieve with 297 micron openings and be retained on a U.S. Standard 140 mesh sieve with 105 micron openings when said particles are tested according to the Sieving Test.

23. The absorbent article of claim 22 wherein at least about 95% of said particles by weight in said absorbent core will pass through a U.S. Standard 50 mesh sieve with 297 micron openings and be retained on a U.S. Standard 140 mesh sieve with 105 micron openings when said particles are tested according to the Sieving Test.

24. The absorbent article of claim 18 wherein said primary structure comprising said absorbent core at least partially comprises a fiber material and said polymer material is mixed with said fiber material.

25. The absorbent structure of claim 24 wherein said fiber material is hydrophilic.

26. The absorbent structure of claim 24 wherein said fiber material comprises wood pulp fibers.

27. The absorbent article of claim 18 wherein said particles are uniformly distributed throughout the absorbent core.

28. The absorbent article of claim 18 or 27 wherein said absorbent core has a density of from about 0.06 g/cm$^3$ to about 0.3 g/cm$^3$.

29. The absorbent article of claim 18 wherein said particles are distributed in a positive gradient through at least a portion of the thickness of said absorbent core.

30. The absorbent article of claim 19 wherein said acquisition zone extends from the top surface of the absorbent core through at least a fraction of the total thickness of the absorbent core, the top surface area of said acquisition zone comprising less than about 50% of the top surface area of the absorbent core.

31. The absorbent article of claim 20 wherein said absorbent core has a top surface area that is from about 0.25 to about 1.0 times that of said absorbent acquisition layer.

32. The absorbent article of claim 20 wherein said absorbent acquisition layer consists essentially of hydrophilic fiber material.

33. The absorbent article of claim 20 wherein said absorbent acquisition layer has a top surface area that is from about 0.25 to about 1.0 times that of the absorbent article.

34. The absorbent article of claim 20 wherein said absorbent acquisition layer comprises chemically stiffened cellulosic fibers.

35. The absorbent article of claim 21 wherein said dusting layer is relatively thinner in thickness than the absorbent core.

36. The absorbent article of claim 18 wherein said absorbent core has a body-facing side and a garment-facing side and further comprises an acquisition patch at least partially comprised of cross-linked cellulose fibers on said body-facing side of said absorbent core.

37. An absorbent article comprising:
a liquid pervious topsheet;
a liquid impervious backsheet joined to said topsheet; and
an absorbent core positioned between said topsheet and said backsheet, said absorbent core comprising a primary structure and a plurality of particles of substantially water insoluble, absorbent, hydrogel-forming, polymer material in said primary structure, said particles of polymer material being formed by solution polymerization methods and distributed in a concentration of between about 35% and about 90% by weight of said absorbent core in at least a 25 square centimeter portion of said absorbent core according to the Weight Percentage Analysis, which particles are of such size that at least about 85% of said particles, by weight, will pass through a U.S. Standard 50 mesh sieve with 297 micron openings and be retained on a U.S. Standard 120 mesh sieve with 125 micron openings when said particles are tested according to the Sieving Test.

38. The absorbent article of claim 37 wherein at least about 90% of said particles by weight in said absorbent core will pass through a U.S. Standard 50 mesh sieve with 297 micron openings and be retained on a U.S. Standard 120 mesh sieve with 125 micron openings when said particles are tested according to the Sieving Test.

39. The absorbent article of claim 38 wherein at least about 95% of said particles by weight in said absorbent core will pass through a U.S. Standard 50 mesh sieve with 297 micron openings and be retained on a U.S. Standard 120 mesh sieve with 125 micron openings when said particles are tested according to the Sieving Test.

40. The absorbent article of claims 37, 38, or 39 wherein said 25 square centimeter portion of said absorbent core comprises between about 50% and about 90% by weight of particles of substantially water-insoluble, absorbent, hydrogel-forming, polymer material.

41. The absorbent article of claims 37, 38, or 39 wherein said 25 square centimeter portion of said absorbent core comprises between about 70% and about 90% by weight of particles of substantially water-insoluble, absorbent, hydrogel-forming, polymer material.

42. An absorbent article comprising: a liquid pervious topsheet; a liquid impervious backsheet joined to said topsheet; and an absorbent core positioned between said topsheet and said backsheet, said absorbent core comprising a primary structure and a plurality of particles of substantially water insoluble, absorbent, hydrogel-forming, polymer material in said primary structure, said particles of polymer material being formed by solution polymerization methods and distributed in a concentration of between about 35% and about 90% by weight of said absorbent core in at least a 25 square centimeter portion of said absorbent core according to the Weight Percentage Analysis, which particles are of such size that at least about 85% of said particles, by weight, will pass through a U.S. Standard 50 mesh sieve with 297 micron openings and be retained on a U.S. Standard 100 mesh sieve with 149 micron openings when said particles are tested according to the Sieving Test.

43. The absorbent article of claim 42 wherein at least about 90% of said particles by weight in said absorbent core will pass through a U.S. Standard 50 mesh sieve with 297 micron openings and be retained on a U.S. Standard 100 mesh sieve with 149 micron openings when said particles are tested according to the Sieving Test.

44. The absorbent article of claim 43 wherein at least about 95% of said particles by weight in said absorbent core will pass through a U.S. Standard 50 mesh sieve with 297 micron openings and be retained on a U.S. Standard 100 mesh sieve with 149 micron openings when said particles are tested according to the Sieving Test.

45. The absorbent article of claims 42, 43, or 44 wherein said 25 square centimeter portion of said absorbent core comprises between about 50% and about 90% by weight of particles of substantially water-insoluble, absorbent, hydrogel-forming, polymer material.

46. The absorbent article of claims 42, 43, or 44 wherein said 25 square centimeter portion of said absorbent core comprises between about 70% and about 90% by weight of particles of substantially water-insoluble, absorbent, hydrogel-forming, polymer material.

* * * * *